(12) United States Patent
Ho et al.

(10) Patent No.: US 10,080,749 B2
(45) Date of Patent: Sep. 25, 2018

(54) MULTI-DRUG THERAPIES FOR TUBERCULOSIS TREATMENT

(71) Applicant: THE REGENTS OF THE UNIVERSITY OF CALIFORNIA, Oakland, CA (US)

(72) Inventors: Chih-Ming Ho, Los Angeles, CA (US); Daniel L. Clemens, Los Angeles, CA (US); Bai-Yu Lee Clemens, Los Angeles, CA (US); Marcus Aaron Horwitz, Los Angeles, CA (US); Aleidy Marlene Silva Vite, Los Angeles, CA (US); Theodore Kee, Los Angeles, CA (US); Xianting Ding, Shanghai (CN)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/523,906

(22) PCT Filed: Nov. 3, 2015

(86) PCT No.: PCT/US2015/058892
§ 371 (c)(1),
(2) Date: May 2, 2017

(87) PCT Pub. No.: WO2016/073524
PCT Pub. Date: May 12, 2016

(65) Prior Publication Data
US 2017/0333427 A1    Nov. 23, 2017

Related U.S. Application Data

(60) Provisional application No. 62/074,508, filed on Nov. 3, 2014, provisional application No. 62/217,306, filed on Sep. 11, 2015.

(51) Int. Cl.
| | | |
|---|---|---|
| *A61K 31/50* | (2006.01) |
| *A61K 31/498* | (2006.01) |
| *A61K 31/133* | (2006.01) |
| *A61K 31/4965* | (2006.01) |
| *A61K 31/44* | (2006.01) |
| *A61K 31/47* | (2006.01) |

(52) U.S. Cl.
CPC .......... *A61K 31/498* (2013.01); *A61K 31/133* (2013.01); *A61K 31/44* (2013.01); *A61K 31/47* (2013.01); *A61K 31/4965* (2013.01)

(58) Field of Classification Search
USPC ........................................................ 514/248
See application file for complete search history.

(56) References Cited

U.S. PATENT DOCUMENTS

| | | |
|---|---|---|
| 2002/0068761 A1 | 6/2002 | Bernstein |
| 2014/0045791 A1 | 2/2014 | Locher et al. |

OTHER PUBLICATIONS

Field et al. Chest, 2003, 124(4):1482-6.*
iDiacon et al. , Lancet, 2012, 380(9846): 986-93.*
Urbanczik R. Chemotherapy, 1980, 26(4): 276-81.*
Conradie et al. (2014), "Clinical Access to Bedaquiline Programme for the Treatment of Drug-Resistant Tuberculosis", S Afr Med J, Mar. 2014, vol. 104(3), pp. 164-166.
International Search Report and Written Opinion for International Application No. PCT/US2015/058892 dated Feb. 9, 2016, 10 pages.
Van Duen et al. (2010) "Short, Highly Effective, and Inexpensive Standardized Treatment of Multidrug-resistant Tuberculosis", Am J Respir Crit Care Med., vol. 182, pp. 684-692.
Wong et al. (2013), "Rising to the challenge: new therapies for tuberculosis", Trends Microbiol. 2013, vol. 21(9), pp. 493-501.
Nuermberger, E.L. et al. (2004) "Moxifloxacin-containing Regimen Greatly Reduces Time to Culture Conversion in Murine Tuberculosis," Am J Respir Crit Care Med 169:421-426.
Tasneen, R. et al. (2011) "Sterilizing Activity of Novel TMC207— and PA-824-Containing Regimens in a Murine Model of Tuberculosis," Antimicrob. Agents Chemother. 55(12):5485-5492.
Williams, K.N. et al. (2009) "Addition of PNU-100480 to First-Line Drugs Shortens the Time Needed to Cure Murine Tuberculosis," Am J Respir Crit Care Med 180:371-376.

\* cited by examiner

*Primary Examiner* — Rei Tsang Shiao
(74) *Attorney, Agent, or Firm* — Foley & Lardner LLP; Antoinette F. Konski; Alice Lee-Dutra

(57) ABSTRACT

The present invention is directed to methods of treating tuberculosis by providing a pharmaceutically effective amount of a combination of drug compounds.

17 Claims, 33 Drawing Sheets

Standard Regimen

| Drug | | mg/kg |
|---|---|---|
| Isoniazid | INH | 25 |
| Rifampin | RIF | 10 |
| Ethambutol | EMB | 100 |
| Pyrazinamide | PZA | 150 |

Enhanced Standard Regimen

| Drug | | mg/kg |
|---|---|---|
| Isoniazid | INH | 25 |
| Rifampin | RIF | 10 |
| Ethambutol | EMB | 100 |
| Pyrazinamide | PZA | 450 |

FSC Regimen I

| Drug | | mg/kg |
|---|---|---|
| Clofazimine | CLZ | 25 |
| Ethambutol | EMB | 100 |
| Prothionamide | PRO | 75 |
| Pyrazinamide | PZA | 450 |

FSC Regimen II A/B

| Drug | | mg/kg |
|---|---|---|
| Clofazimine | CLZ | 25 |
| Ethambutol | RIF | 100 |
| TMC-207 | TMC | 16.7 |
| Pyrazinamide | PZA | 150 A<br>450 B |

FIG. 12

Efficacy

| Group | Regimen | Drugs | Dose (mg/kg) 5 days/week | Mice | \-2 | 0 | 2 | 3 | 4 | 6 | 8 |
|---|---|---|---|---|---|---|---|---|---|---|---|
| A* | Untreated | No drug | not apply | 7 | 2 | 5 | | | | | |
| A | Sham treated | No drug | not apply | 25 | | | 5 | 5 | 5 | 5 | 5 |
| B | Standard Regimen | INH/RIF/EMB/PZA | 25/10/100/150 | 25 | | | 5 | 5 | 5 | 5 | 5 |
| C | Enhanced Standard Regimen | INH/RIF/EMB/PZA | 25/10/100/150 | 15 | | | | 5 | 5 | | 5 |
| D | FSC Regimen I | CLZ/EMB/PRO/PZA | 25/100/75/450 | 15 | | | | 5 | 5 | 5 | |
| E | FSC Regimen IIA | CLZ/EMB/TMC/PZA | 25/100/16.5/150 | 20 | | | 5 | 5 | 5 | 5 | 5 |
| F | FSC Regimen IIB | CLZ/EMB/TMC/PZA | 25/100/16.7/450 | 10 | | | 5 | 5 | | 5 | |

Number of mice euthanized per group — Week

Relapse

| Group | Regimen | Drugs | Dose (mg/kg) 5 days/week | Mice | Treatment (Duration) | Relapse Assessment (Time after Treatment) |
|---|---|---|---|---|---|---|
| H | FSC Regimen IIA | CLZ/EMB/TMC/PZA | 25/100/16.7/150 | 8 | 3 weeks | 3 months |
| I | FSC Regimen IIA | CLZ/EMB/TMC/PZA | 25/100/16.7/150 | 7 | 4 weeks | 3 months |
| J | FSC Regimen IIA | CLZ/EMB/TMC/PZA | 25/100/16.7/150 | 5 | 6 weeks | 3 months |

FIG. 13

Efficacy at 3 weeks

| Mouse # | Lung CFU* |
|---|---|
| 1 | 12.5 |
| 2 | 12 |
| 3 | 12 |
| 4 | 25 |
| 5 | 13 |

*Lung CFU = $\dfrac{\text{CFU or 0.5 if CFU is 0}}{\text{Volume Plated}} \times \text{Total Organ volume}$

Relapse after 3 months

| Mouse # | Lung Total CFU* | Spleen Total CFU* |
|---|---|---|
| 1 | 3635 | 127 |
| 2 | 9333 | 0 |
| 3 | 1120 | 0 |
| 4 | 0 | 0 |
| 5 | 1 | 0 |
| 6 | 0 | 0 |
| 7 | 0 | 0 |
| 8 | 0 | 0 |

* Entire organ plated

FIG. 16

Efficacy at 4 weeks

| Mouse # | Lung CFU* |
|---|---|
| 1 | 2.2 |
| 2 | 2.3 |
| 3 | 2.75 |
| 4 | 9 |
| 5 | 2.2 |

*Lung CFU = $\frac{CFU \text{ or } 0.5 \text{ if } CFU \text{ is } 0}{Volume\ Plated} \times Total\ Organ\ volume$ (All agar plates but Mouse #4 had 0 CFU)

Relapse after 3 months

| Mouse # | Lung Total CFU* | Spleen Total CFU* |
|---|---|---|
| 1 | 0 | 0 |
| 2 | 0 | 0 |
| 3 | 0 | 0 |
| 4 | 0 | 0 |
| 5 | 0 | 0 |
| 6 | 0 | 0 |
| 7 | 0 | 0 |

*Entire organ plated*

FIG. 17

Efficacy at 6 weeks

| Mouse # | Lung CFU* |
|---|---|
| 1 | 2.3 |
| 2 | 2.3 |
| 3 | 2.3 |
| 4 | 2.4 |
| 5 | 3.0 |

*Lung CFU = $\dfrac{CFU \text{ or } 0.5 \text{ if } CFU \text{ is } 0}{Volume\ Plated} \times Total\ Organ\ volume$ (All agar plates had 0 CFU)

Relapse after 3 months

| Mouse # | Lung Total CFU* | Spleen Total CFU* |
|---|---|---|
| 1 | 0 | 0 |
| 2 | 0 | 0 |
| 3 | 0 | 0 |
| 4 | 0 | 0 |
| 5 | 0 | 0 |

* Entire organ plated

FIG. 18

| Grp | Regimen | Drugs | Dose(mg/kg) | Mice | -2 | 0 | 2 | 3 | 4 | 6 | 8 | 12 | 16 | 20 | 24 |
|---|---|---|---|---|---|---|---|---|---|---|---|---|---|---|---|
| A* | None | None | - | 8 | 3 | 5 | | | | | | | | | |
| A | Sham treated | None | - | 40 | | 5 | | 5 | 5 | 5 | 5 | 5 | 5 | 5 | 5 |
| B | Standard Regimen | INH/RIF/EMB/PZA >8 Wks: INH/RIF | 25/10/100/150 5 days/week | 55 | | | | 5 | 5 | 5 | 5 | 5 5* | 5 5* | 5 5* | 5 |
| C | Enhanced Standard Regimen | INH/RIF/EMB/PZA >8 Wks: INH/RIF | 25/10/100/450 5 days/week | 55 | | | | 5 | | | 5 | 5 5* | 5 5* | 5 5* | 5 |
| D | FSC Regimen I | CLZ/EMB/PRO/PZA | 25/100/75/450 5 days/week | 20 | | | | | | | 5 5* | 5 5* | | | |
| E | FSC Regimen IIC | CLZ/EMB/TMC/PZA | 25/100/30/150 5 days/week | 30 | | | | 5 5* | 5 5* | 5 5* | | | | | |
| F | FSC Regimen IIC | CLZ/EMB/TMC/PZA | 25/100/30/450 Daily | 20 | | | 5 5* | 5 5* | | | | | | | |

Week (Number of Mice Euthanized per Group)

*Relapse

FIG. 19

MULTI-DRUG THERAPIES FOR TUBERCULOSIS TREATMENT

CROSS-REFERENCE TO RELATED APPLICATIONS

This application is a National Stage Entry of International Application No. PCT/US2015/058892, filed Nov. 3, 2015, which claims the benefit of U.S. Provisional Application No. 62/074,508, filed Nov. 3, 2014, and U.S. Provisional Application No. 62/217,306, filed Sep. 11, 2015, each of which is incorporated by reference herein in its entirety.

BACKGROUND

The use of drug combinations possesses an important advantage over single drug therapy. Monotherapies often lead to disease recurrence and subsequent ineffectiveness of standard treatment due to drug resistance development. Multi-drug therapies are now the standard treatment for multiple diseases, but their development has involved arduous empirical testing. The design of such therapies is quite challenging since the interactions between drugs are not well understood, as the crossover between the affected cellular pathways is quite difficult to comprehend. Furthermore, combining several drugs at different possible concentrations or doses yields a large testing parametric space, which makes the search of an optimal combination a major challenge. Therefore, there is a need to use a different approach to develop multi-drug therapies.

It is against this background that a need arose to develop the embodiments described in this disclosure.

SUMMARY OF THE DISCLOSED SUBJECT MATTER

In certain aspects, the present invention is directed to pharmaceutical composition comprising a pharmaceutically effective amount of a combination of (a) clofazimine, (b) ethambutol, (c) pyrazinamide, and (d) prothionamide or bedaquiline. In some embodiments, the pharmaceutical composition comprises, or alternatively consists essentially of, or yet further consists of the combination of: (a) clofazimine, (b) ethambutol, (c) pyrazinamide, and (d) bedaquiline. In other embodiments, the pharmaceutical composition comprises, or alternatively consists essentially of, or yet further consists of the combination of: (a) clofazimine, (b) ethambutol, (c) pyrazinamide, and (d) prothionamide. In one aspect, the compounds are added to a carrier such as a pharmaceutically acceptable carrier.

Other aspects of the present disclosure include a method of treating tuberculosis in a subject in need thereof, comprising, or alternatively consists essentially of, or yet further consists of, administering to the patient a therapeutically effective amount of a drug combination comprising: (a) clofazimine, (b) ethambutol, (c) pyrazinamide, and (d) prothionamide or bedaquiline. In some embodiments, the combination comprises, or alternatively consists essentially of, or yet further consists of: (a) clofazimine, (b) ethambutol, (c) pyrazinamide, and (d) bedaquiline. In other embodiments of the methods, the combination comprises, or alternatively consists essentially of, or yet further consists of (a) clofazimine, (b) ethambutol, (c) pyrazinamide, and (d) prothionamide. In some embodiments, one or more of (a)-(d) in the combination is administered sequentially. Other embodiments, include where the one or more of (a)-(d) is administered concurrently. In some embodiments the subject is a mammal, for example, a human. In some embodiments, the drug combination consists of (a) clofazimine, (b) ethambutol, (c) pyrazinamide, and (d) prothionamide or bedaquiline. In other embodiments, the combination consists of (a) clofazimine, (b) ethambutol, (c) pyrazinamide, and (d) bedaquiline. In other embodiments, the combination consists of (a) clofazimine, (b) ethambutol, (c) pyrazinamide, and (d) prothionamide. In some embodiments, the tuberculosis is caused by *Mycobacterium tuberculosis*. In some embodiments, the tuberculosis is Multi-drug resistant TB. In some embodiments, the tuberculosis is Extensively drug-resistant TB.

BRIEF DESCRIPTION OF THE DRAWINGS

FIG. 12 shows drugs and drug doses in each combinational drug regimen of an embodiment.

FIG. 13 shows the scheme of Mouse in vivo data for Example 3.

FIG. 16 shows Lung burden 3 days (Efficacy) and 3 months (Relapse) after treatment with FSC Regimen IIA for 3 weeks.

FIG. 17 shows Lung burden 3 days (Efficacy) and 3 months (Relapse) after treatment with FSC Regimen IIA for 4 weeks.

FIG. 18 shows Lung burden 3 days (Efficacy) and 3 months (Relapse) after treatment with FSC Regimen IIA for 6 weeks.

FIG. 19 shows a scheme of Mouse in vivo Experiment 4.

DETAILED DESCRIPTION

Figure 1:
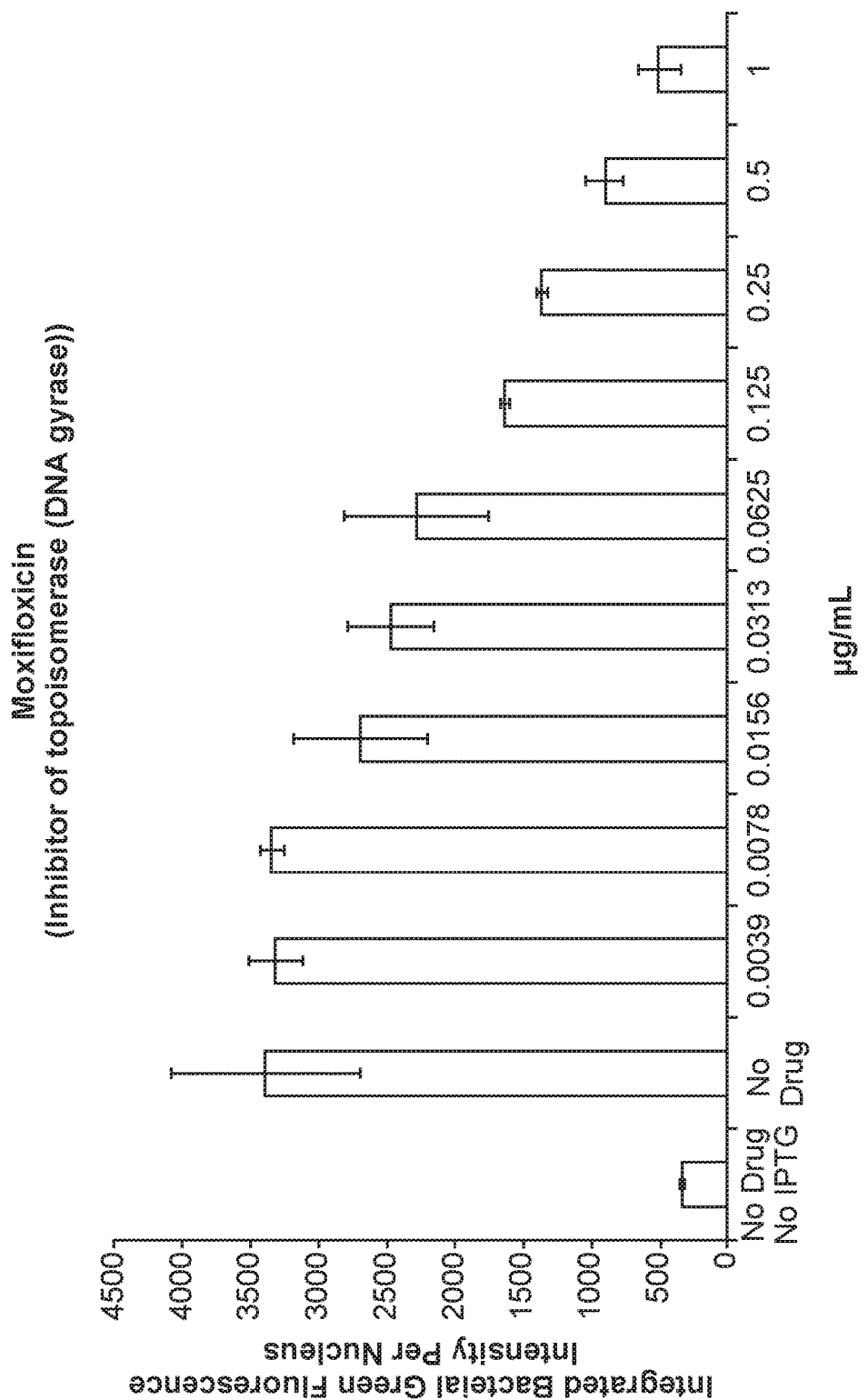
FIG. 1 shows a Dose-response for moxifloxacin in the Inhibition Assay.

Currently, treatment for Tuberculosis (TB) depends upon the drug sensitivity of the infecting strain of *Mycobacterium tuberculosis* and patient demographic (e.g., child, adult, pregnant, HIV-positive, and so forth). The two main classifications of TB treatment are "first-line" and "second-line". First-line treatment of drug-sensitive TB is a 4-drug regimen: isoniazid (INH), rifampin (RIF), pyrazinamide (PZA), and ethambutol (EMB). Second-line treatments used to treat drug-resistant TB utilize 3-5 other drugs in combination: aminoglycosides (amikacin (AMK), kanamycin (KM), and so forth), polypeptides capreomycin, viomycin, and so forth), thioamides (e.g., ethioamide, prothioamide (PRO), and so forth), fluoroquinolones (e.g., ciprofloxacin (CIP), levofloxacin, moxifloxacin (MXF), and so forth), and cycloserine. There also are combination drugs or fixed-dose combinations (FDCs) used to help reduce the number of pills to be taken by patients during the TB treatment period. Examples of FDCs used for TB treatment include Rifater [isoniazid (INH), pyrazinamide (PZA), and rifampicin (RIF)] and Rifamate [isoniazid (INH) and rifampin (RIF)].

TB strains that are resistant to anti-TB drugs are increasingly being encountered. Approximately 450,000 people developed multi-drug resistant TB in 2012; half of the reported numbers were in India, China, and Russia. Multi-drug resistant TB (MDR-TB) is a categorization of strains of TB that are resistant to at least both isoniazid and rifampicin. MDR-TB arises from inappropriate treatment such as: use of poor quality medicines, administration of improper treatment regimens, and failing to ensure the patient has completed the whole course of treatment. Because MDR-TB is due to bacteria resistant to the two most powerful first-line anti-TB drugs, MDR-TB patients are then treated with first-line drugs to which the strain is sensitive plus several second-line drugs. However, second-line treatment options have their own sets of limitations and drawbacks: extensive chemotherapy, high cost, severe adverse drug reactions, and possible lack of availability. Furthermore, treatment with second-line drugs can lead to more severe drug resistance similar to the inappropriate treatment causing MDR-TB. Extensively drug-resistant TB (XDR-TB) is specified as MDR-TB that is additionally resistant to several other classes of anti-TB drugs including the most effective second-line anti-TB drugs. It is estimated that about 9.6% of reported MDR-TB cases are XDR-TB.

Embodiments of this disclosure are directed to a combination of drugs in respective doses, uses thereof for treating tuberculosis, and a method for determining the optimum drug doses in the combination. In some embodiments, the method involves three stages. First, the optimal drug-dose combinations are determined on the basis of in vitro studies on the efficacy of various drug-dose combinations in inhibiting and in killing *Mycobacterium tuberculosis*, using a Feedback System Control (FSC) optimization scheme. Second, optimal combinations, namely those more efficacious or potent than the standard regimen of isoniazid (INH), rifampin (RIF), ethambutol (EMB) and pyrazinamide (PZA), are tested in a mouse model of pulmonary TB to determine the optimal drug doses in vivo in the mouse, using the FSC scheme. Finally, corresponding human doses can be extrapolated from mouse doses using drug dose extrapolation techniques and mouse and human pharmacokinetic data for the drugs after oral administration.

i. Drug Combinations

The present disclosure includes various combinations of known drugs. The combinations show improved potency against, e.g., various forms of tuberculosis compared to conventional treatments. In some embodiments, multiple optimal drug-dose combinations are determined on the basis of in vitro studies and FSC analysis. Certain embodiments of drug combinations have been evaluated on the basis of in vitro TB treatment tests, and have been shown to perform equally or better than the standard regimen (See Working Example Section including in vitro studies).

In some embodiments the drug combination is selected from one of the following (1) Clofazimine (CLZ), ethambutol (EMB), 4-aminosalicyclic acid (PAS), and bedaquiline (TMC207).
(2) Clofazimine (CLZ), ethambutol (EMB), 4-aminosalicyclic acid (PAS), and rifampicin (RIF).
(3) Clofazimine (CLZ), ethambutol (EMB), 4-aminosalicyclic acid (PAS), and pyrazinamide (PZA).
(4) Clofazimine (CLZ), ethambutol (EMB), 4-aminosalicyclic acid (PAS), and prothionamide (PRO).
(5) Clofazimine (CLZ), ethambutol (EMB), prothionamide (PRO), and pyrazinamide (PZA).
(6) Clofazimine (CLZ), ethambutol (EMB), prothionamide (PRO), and rifampicin (RIF).
(7) Clofazimine (CLZ), ethambutol (EMB), and prothionamide (PRO).
(8) Clofazimine (CLZ), ethambutol (EMB), and pyrazinamide (PZA).
(9) Clofazimine (CLZ), ethambutol (EMB), pyrazinamide (PZA), and bedaquiline (TMC207).
(10) Clofazimine (CLZ), ethambutol (EMB), pyrazinamide (PZA), and rifampicin (RIF).
(11) Clofazimine (CLZ), ethambutol (EMB), rifampicin (RIF), and bedaquiline (TMC207).
(12) Clofazimine (CLZ), ethambutol (EMB), and bedaquiline (TMC207).
(13) Clofazimine (CLZ), prothionamide (PRO), rifampicin (RIF), and bedaquiline (TMC207).
(14) Clofazimine (CLZ), prothionamide (PRO), pyrazinamide (PZA), and bedaquiline (TMC207).
(15) Clofazimine (CLZ), 4-aminosalicyclic acid (PAS), prothionamide (PRO), and bedaquiline (TMC207).
(16) Ethambutol (EMB), prothionamide (PRO), pyrazinamide (PZA), and bedaquiline (TMC207).
(17) Ethambutol (EMB), prothionamide (PRO), pyrazinamide (PZA), and rifampin (RIF).
(18) Ethambutol (EMB), prothionamide (PRO), and pyrazinamide (PZA).
(19) Ethambutol (EMB), prothionamide (PRO), and bedaquiline (TMC207).
(20) Ethambutol (EMB), prothionamide (PRO), rifampicin (RIF), and bedaquiline (TMC207).
(21) Ethambutol (EMB), 4-aminosalicyclic acid (PAS), prothionamide (PRO), and bedaquiline (TMC207).
(22) Ethambutol (EMB), 4-aminosalicyclic acid (PAS), prothionamide (PRO), and rifampicin (RIF).
(23) Clofazimine (CLZ), ethambutol (EMB), prothionamide (PRO), and bedaquiline (TMC207).
(24) Clofazimine (CLZ), prothionamide (PRO), and bedaquiline (TMC207).
(25) Clofazimine (CLZ), prothionamide (PRO), and pyrazinamide (PZA)
(26) Clofazimine (CLZ), ethambutol (EMB), prothionamide (PRO), and pyrazinamide (PZA.).
(27) CLZ, PRO, PZA.
(28) CLZ, EMB, PZA.
(29) CLZ, PRO, EMB.

In some embodiments, the drug combination is selected from one of the following combinations of Table 1.

TABLE 1

Individual embodiments of drug combinations evaluated on the basis of in vitro TB treatment tests

| | | | | |
|---|---|---|---|---|
| 1. | Clofazimine (CLZ) | Pyrazinamide (PZA) | SQ109 | Bedaquiline (TMC207) |
| 2. | Clofazimine (CLZ) | Prothionamide (PRO) | Pyrazinamide (PZA) | SQ109 |
| 3. | Clofazimine (CLZ) | PA824 | Pyrazinamide (PZA) | SQ109 |
| 4. | Clofazimine (CLZ) | Ethambutol (EMB) | PA824 | Bedaquiline (TMC207) |
| 5. | Clofazimine (CLZ) | Prothionamide (PRO) | SQ109 | Bedaquiline (TMC207) |
| 6. | Clofazimine (CLZ) | PA824 | SQ109 | Bedaquiline (TMC207) |
| 7. | Clofazimine (CLZ) | Ethambutol (EMB) | SQ109 | Bedaquiline (TMC207) |
| 8. | Clofazimine (CLZ) | Prothionamide (PRO) | Rifampin (RIF) | SQ109 |
| 9. | Clofazimine (CLZ) | Ethambutol (EMB) | PA824 | Prothionamide (PRO) |
| 10. | Clofazimine (CLZ) | PA824 | Prothionamide (PRO) | SQ109 |
| 11. | Clofazimine (CLZ) | Ethambutol (EMB) | Pyrazinamide (PZA) | SQ109 |
| 12. | Clofazimine (CLZ) | Pyrazinamide (PZA) | Rifampin (RIF) | SQ109 |
| 13. | Clofazimine (CLZ) | Ethambutol (EMB) | Prothionamide (PRO) | SQ109 |
| 14. | Clofazimine (CLZ) | 4-aminosalicyclic acid (PAS) | Pyrazinamide (PZA) | SQ109 |
| 15. | Clofazimine (CLZ) | Ethambutol (EMB) | PA824 | SQ109 |
| 16. | Clofazimine (CLZ) | Rifampin (RIF) | SQ109 | Bedaquiline (TMC207) |
| 17. | Clofazimine (CLZ) | Ethambutol (EMB) | PA824 | Pyrazinamide (PZA) |
| 18. | Clofazimine (CLZ) | Ethambutol (EMB) | Rifampin (RIF) | SQ109 |
| 19. | Clofazimine (CLZ) | 4-aminosalicyclic acid (PAS) | SQ109 | Bedaquiline (TMC207) |
| 20. | Clofazimine (CLZ) | PA824 | Rifampin (RIF) | SQ109 |
| 21. | Clofazimine (CLZ) | Ethambutol (EMB) | PA824 | Rifampin |
| 22. | Clofazimine (CLZ) | Prothionamide (PRO) | Rifampin (RIF) | SQ109 |
| 23. | Clofazimine (CLZ) | 4-aminosalicyclic acid (PAS) | Prothionamide (PRO) | SQ109 |
| 24. | Ethambutol (EMB) | Pyrazinamide (PZA) | SQ109 | Bedaquiline (TMC207) |
| 25. | Ethambutol (EMB) | Prothionamide (PRO) | Rifampin (RIF) | SQ109 |
| 26. | Ethambutol (EMB) | Prothionamide (PRO) | SQ109 | Bedaquiline (TMC207) |
| 27. | Ethambutol (EMB) | PA824 | SQ109 | Bedaquiline (TMC207) |
| 28. | Ethambutol (EMB) | PA824 | Prothionamide (PRO) | Rifampin (REF) |
| 29. | Ethambutol (EMB) | Rifampin (RIF) | SQ109 | Bedaquiline (TMC207) |
| 30. | PA824 | Pyrazinamide (PZA) | SQ109 | Bedaquiline (TMC207) |
| 31. | PA824 | Prothionamide (PRO) | Pyrazinamide (PZA) | SQ109 |
| 32. | PA824 | Prothionamide (PRO) | Rifampin (RIF) | SQ109 |
| 33. | Prothionamide (PRO) | Pyrazinamide (PZA) | SQ109 | Bedaquiline (TMC207) |
| 34. | Prothionamide (PRO) | Pyrazinamide (PZA) | Rifampin (RIF) | SQ109 |
| 35. | Prothionamide (PRO) | Rifampin (RIF) | SQ109 | Bedaquiline (TMC207) |
| 36. | Clofazimine (CLZ) | Pyrazinamide (PZA) | SQ109 | |
| 37. | Clofazimine (CLZ) | SQ109 | Bedaquiline (TMC207) | |
| 38. | Clofazimine (CLZ) | Prothionamide (PRO) | SQ109 | |

Furthermore, in some embodiments, ethambutol (EMB) and SQ109 are shown to have similarities in their behavior and interactions (See Section on EMB and SQ109); thus they can be interchanged in certain embodiments of the disclosure. The following list of individual embodiments of drug combinations is derived from the previous list, in which either ethambutol or SQ109 were replaced by its counterpart.

| | | | |
|---|---|---|---|
| 39. Clofazimine (CLZ) | Ethambutol (FMB) | PA824 | Pyrazinamide (PZA) |
| 40. Clofazimine (CLZ) | PA824 | SQ109 | Bedaquiline (TMC207) |
| 41. Clofazimine (CLZ) | Ethambutol (EMB) | PA824 | Bedaquiline (TMC207) |
| 42. Clofazimine (CLZ) | Ethambutol (EMB) | Prothionamide (PRO) | Rifampin (RIF) |
| 43. Clofazimine (CLZ) | PA824 | Prothionamide (PRO) | SQ109 |
| 44. Clofazimine (CLZ) | Ethambutol (ENB) | PA824 | Prothionamide (PRO) |
| 45. Clofazimine (CLZ) | PA824 | Pyrazinamide (PZA) | SQ109 |
| 46. Clofazimine (CLZ) | Ethambutol (EMB) | PA824 | Rifampin (RIF) |

In the case of two of the most potent combinations, the optimal drug doses in a mouse model of pulmonary tuberculosis are determined, and, surprisingly, the combination is demonstrated to be superior to the standard regimen. Translating this to human doses involves extrapolation of pharmacokinetics of the drugs in mice and humans.

Some individual embodiments of drug combinations were shown to be superior to the standard regime (See Sections on in vivo studies):

| | | | |
|---|---|---|---|
| 47. Clofazimine (CLZ) | Ethambutol (EMB) | Prothionamide (PRO) | Pyrazinamide (PZA) |
| 48. Clofazimine (CLZ) | Ethambutol (EMB) | Bedaquiline (TMC207) | Pyrazinamide (PZA) |

In some embodiments, one or more of the drug combinations provide at least one of a number of benefits, including one or more of the following. First, the drug combinations are treatment combinations that can have higher efficacy than other drug combinations used for TB treatment. Second, the drug combinations provide alternative combinations for the treatment of drug-resistant TB, and also allows faster treatment of drug-resistant TB. Since many of the drug combinations do not include INH and RIF, alternative regimens can be developed that are suitable for the treatment of many cases of MDR-TB. Surprisingly, even though many of the drug combinations do not include the two most powerful first-Line anti-TB drugs, INH and RIF, those combinations are shown to be superior to the standard regimen. Moreover, because, in some embodiments, the regimens do not include, or can omit, fluoroquinolones or aminoglycosides, the regimens also can be useful for treatment of many cases of XDR-TB. Third, current drug treatment regimen generally requires 6-8 months of treatment. Treatment of drug-resistant strains takes even longer, typically 24 months. Because treatment is so prolonged, patient compliance is often poor. Poor patient compliance increases the likelihood of drug resistance developing. The proposed drug-dose combinations of this disclosure allow more rapid and more efficacious treatment of both drug-sensitive and drug-resistant TB and greater patient compliance. In addition, the optimal drug combinations can be used to rapidly treat latent TB, which currently involves 3-9 months of treatment.

ii. Methods of Treatment

Some embodiments of the present disclosure include methods of treating tuberculosis in a subject in need thereof, comprising administering to the patient a therapeutically effective amount of a drug combination described herein. For example, in some embodiments, the combination comprises, or alternatively consists essentially of, or yet further consists of: (a) clofazimine, (b) ethambutol, (c) pyrazinamide, and (d) prothionamide or bedaquiline. In some embodiments the combination comprises, or alternatively consists essentially of, or yet further consists one of the combinations selected from groups 1-48 in Table 1. In some embodiments, the combination consists of one of the combinations selected from groups 1-48 in Table 1. In some embodiments, the methods of treating tuberculosis in a subject in need thereof, do not comprise administering to the patient SQ109. In other embodiments, the methods of treating tuberculosis in a subject in need thereof, comprise administering to the patient SQ109.

The drug combination used in the methods of the present disclosure are administered sequentially or concurrently. In some embodiments, one or two or three of the compounds of the selected combination are delivered sequentially. In some embodiments, one or two or three of the compounds of the selected combination are delivered concurrently.

The administration schedule of the present methods may be manner that provides a desirable therapeutic effect. For example, in some embodiments the combination is administered once a day, twice a day or three times a day. In some embodiments, administration is continued for 2 or 4 or 6 or 8 weeks, or one, two, three, four or five months, or any value therein between. In some embodiments, the treatment regimen requires less than 6 months of treatment, or less than 9, 12, 15, 18, 21 or 24 moths for drug-resistant strains.

In some embodiments, the subject in need thereof is a mammal. The mammal can be any mammal, including, for example, farm animals, such as sheep, pigs, cows, and horses; pet animals, such as dogs and cats; laboratory animals, such as rats, mice and rabbits. In one embodiment, the mammal is a human.

In some embodiments, the tuberculosis treated is caused by *Mycobacterium tuberculosis*. In other embodiments, the tuberculosis treated is caused by other species in the *Mycobacterium tuberculosis* complex. In some embodiments, the tuberculosis is drug-sensitive TB or Multi-drug resistant TB (MDR-TB) or Extensively drug-resistant TB (XDR-TB).

MDR-TB is a categorization of strains of TB that are resistant to at least both isoniazid and rifampicin. MDR-TB arises from inappropriate treatment such as: use of poor quality medicines, administration of improper treatment regimens, and failing to ensure the patient has completed the whole course of treatment.

XDR-TB is specified as MDR-TB that is additionally resistant to several other classes of anti-TB drugs including the most effective second-line anti-TB drugs. In some embodiments, the XDR-TB is resistant to one or more second line drugs selected from the groups consisting of aminoglycosides (amikacin (AMK), kanamycin (KM), and so forth), polypeptides (e.g., capreomycin, viomycin, and so forth), thioamides (e.g., ethioamide, prothioamide (PRO), and so forth), fluoroquinolones (e.g., ciprofloxacin (CIP), levofloxacin, moxifloxacin (MXF), and so forth), and cycloserine. It is estimated that about 9.6% of reported MDR-TB cases are XDR-TB.

iii. Pharmaceutical Formulations

Embodiments of this disclosure can be implemented as kits of drug combinations or as FDCs along with a pharmaceutically acceptable carrier or excipient. For example, drugs in optimal 3-drug or 4-drug combinations can be combined into a single solid dose formulation tier treating TB, where doses of the drugs in the combinations are in a proper ratio to each other.

For oral administration, liquid or solid dose formulations may be used. Some examples of oral dosage formulations include tablets, gelatin capsules, pills, troches, elixirs, suspensions, syrups, wafers, chewing gum and the like. The compounds can be mixed with a suitable pharmaceutical carrier (Vehicle) or excipient as understood by practitioners in the art. Examples of carriers and excipients include starch, milk, sugar, certain types of clay, gelatin, lactic acid, stearic acid or salts thereof, including magnesium or calcium stearate, talc, vegetable fats or oils, gums and glycols.

For systemic, intracerebroventricular, intrathecal, topical, intravenous, intranasal, subcutaneous, intramuscular, or transdermal administration, formulations of the compounds useful in the methods of the present technology may utilize conventional diluents, carriers, or excipients etc such as are known in the art can be employed to deliver the compounds. For example, the formulations may comprise one or more of the following: a stabilizer, a surfactant (such as a nonionic, ionic, anionic, or zwitterionic surfactant), and optionally a salt and/or a buffering agent. The compound may be delivered in the form of a solution, suspension, or in a reconstituted lyophilized form.

In some embodiments, the stabilizer may, for example, be an amino acid, such as for instance, glycine; or an oligosaccharide, such as for example, sucrose, trehalose, lactose or a dextran. Alternatively, the stabilizer may be a sugar alcohol, such as for instance, mannitol; or a combination thereof. Other stabilizers may include Beeswax, butylated hydroxytoluene, citric acid, ethyl vanillin, gelatin, glycerin, iron oxide, lecithin, p-methoxy acetophenone, parabens, plant oils, and propylene glycol. In some embodiments, the stabilizer or combination of stabilizers constitutes from about 0.1% to about 10% weight for weight of the compound.

In some embodiments, the surfactant is a nonionic surfactant, such as a polysorbate. Some examples of suitable surfactants include polysorbates (e.g., Tween20, Tween80); a polyethylene glycol or a polyoxyethylene polyoxypropylene glycol, such as Pluronic F-68 at from about 0.001% (w/v) about 10% (w/v).

A salt or buffering agent may be any salt or buffering agent, such as for example, sodium chloride, or sodium/potassium phosphate, respectively. In certain embodiments, the buffering agent maintains the pH of the pharmaceutical composition in the range of about 5.5 to about 7.5. The salt and/or buffering agent is also useful to maintain the osmolality at a level suitable for administration to a human or an animal. In some embodiments, the salt or buffering agent is present at a roughly isotonic concentration of about 150 mM to about 300 mM.

The formulations of the compounds useful in the methods of the present technology may additionally comprise one or more conventional additives. Some examples of such additives include a solubilizer such as, for example, glycerol or hydroxypropyl-cyclodextrin; an antioxidant such as for example, benzalkonium chloride (a mixture of quaternary ammonium compounds, known as "quats"), benzyl alcohol, chloretone or chlorobutanol; anaesthetic agent such as for example a morphine derivative; or an isotonic agent etc., such as described above. As a further precaution against oxidation or other spoilage, the pharmaceutical compositions may be stored under nitrogen gas in vials sealed with impermeable stoppers.

In some embodiments, the formulations of the compounds useful in the methods of the present technology are contained in a single vehicle (e.g., a single oral dosage form). For example, the pharmaceutical composition comprising a pharmaceutically effective amount of a combination of the compounds useful in the methods of the present technology (e.g., (a) clofazimine, (b) ethambutol, (c) pyrazinamide, and (d) prothionamide or bedaquiline or any combination disclosed herein) in a single oral dosage formulation (e.g., a single tablet, gelatin capsule, pill, troche, elixir, suspension, etc.).

iv. Feedback System Control (FSC) Optimization Scheme

Stimulations can be applied to direct a complex system toward a desired state, such as applying drugs to treat a patient. The types and the amplitudes (e.g., doses) of applying these stimulations are part of the input parameters that can affect the efficiency in bringing the system toward the desired state. However, N types of different drugs with M doses for each drug will result in $M^N$ possible drug-dose combinations. To identify an optimized or even near optimized combination by multiple tests on all possible combinations is prohibitive in practice. For example, it is not practical to perform all the possible drug-dose combinations in in vitro or in vivo tests for finding an effective drug-dose combination as the number of drugs and doses increase.

Embodiments of this disclosure apply a technique that allows a rapid search for optimized combinations of input parameters to guide multi-dimensional (or multivariate) systems with multiple input parameters toward their desired states. The technique is comprised of a multi-dimensional complex system whose state is affected by input parameters along respective dimensions of a multi-dimensional parameter space. In some embodiments, the technique can efficiently operate on a large pool of input parameters (e.g., a drug pool), where the input parameters can involve complex interactions both among the parameters and with the complex system. A search technique can be used to identify at least a subset, or all, optimized combinations or sub-combinations of input parameters that produce desired states of the complex system. Taking the case of combinational drugs, for example, a large number of drugs can be evaluated to rapidly identify optimized combinations, ratios, and doses of drugs. A, parameter space sampling technique (e.g., an experimental design methodology) can guide the selection of a minimal or reduced number of tests to expose salient features of the complex system being evaluated, and to reveal a combination or sub-combination of input parameters of greater significance or impact in affecting a state of the complex system.

Embodiments of this disclosure are based on a surprising finding that a response of a complex system to multiple input parameters can be represented by a low order equation, such as a second order (or quadratic) equation, although a first order (or linear) equation as well as a third order (or cubic) equation are also contemplated as possible low order equations. Also, higher order equations are contemplated for other embodiments. Taking the case of combinational drugs, fir example, a drug efficacy E can be represented as a function of drug doses as follows:

$$E = E_0 + \sum_i a_i C_i + \sum_{i,j} a_{ij} C_i C_j + O(C_i C_j C_k)$$

where $C_i$ is a dose of an $i^{th}$ drug from a pool of N total drugs, $E_0$ is a constant representing a baseline efficacy, $a_i$ is a constant representing a single drug efficacy coefficient, $a_{ij}$ is a constant representing a drug-drug interaction coefficient, and the summations run through N, if cubic and other higher order terms are omitted, then the drug efficacy E can be represented by a quadratic model as a function of the drug doses $C_i$. As noted above, other models, including ternary and higher order models or the use of linear regression model, are also contemplated. Also, although a specific example of combinational drugs is used, it should be noted that the above equation more generally can be used to represent a wide variety of other complex systems as a function of multiple input parameters.

For the case of N=1 (a pool of 1 drug), then:

$$E = E_0 + a_1 C_1 + a_{11} C_1 C_1$$

with a total of three constants, $E_0$, $a_1$, and $a_{11}$.

For the case of N=2 (a pool of 2 drugs), then:

$$E = E_0 + a_1 C_1 + a_2 C_2 + a_{12} C_1 C_2 + a_{11} C_1 C_1 + a_{22} C_2 C_2$$

with a total of six constants, $E_0$, $a_1$, $a_2$, $a_{12}$, $a_{11}$, and $a_{22}$.

More generally for N total drugs, a total number of constants m is $1+2N+(N(N-1))/2$. If one drug dosage is kept constant in the study, the number of constants in can be further reduced to $1+2(N-1)+((N-1)(N-2))/2$, for N>1. Table 2 below sets forth a total number of constants in a quadratic model of drug efficacy as a function of a total number drugs in a pool of drugs being evaluated.

TABLE 2

| Drugs (N) | Constants (m) | Constants (m) (if one drug dosage is kept constant) |
|---|---|---|
| 1 | 3 | — |
| 2 | 6 | 3 |
| 3 | 10 | 6 |
| 4 | 15 | 10 |
| 5 | 21 | 15 |
| 6 | 28 | 21 |

By leveraging this surprising finding, a relatively small number of in vitro or in vivo tests can be conducted to model an efficacy-dose response surface, and this input/output model can be used to identify optimized drug-dose combinations. In some embodiments, the tests can be conducted in parallel in a single study, thereby greatly enhancing the speed and lowering labor and costs compared with current drug screening.

Taking the case of the quadratic model of drug efficacy E, for example, different combinations of the drug doses $C_i$ can be selected for respective in vivo tests as follows:

$$E^1 = E_0 + \sum_i a_i C_i^1 + \sum_{i,j} a_{ij} C_i^1 C_j^1$$

$$E^2 = E_0 + \sum_i a_i C_i^2 + \sum_{i,j} a_{ij} C_i^2 C_j^2$$

...

$$E^n = E_0 + \sum_i a_i C_i^n + \sum_{i,j} a_{ij} C_i^n C_j^n$$

where $E^k$ is an efficacy observed or measured in a $k^{th}$ test from a total of n tests, and $C_i^k$ is a dose of an $i^{th}$ drug applied in the $k^{th}$ test. From the n tests, the in constants $E_0$, $a_i$, and $a_{ij}$ can be derived, with n≥m, namely with the number of tests being the same as, or greater than, the number of constants in the quadratic model. In some embodiments, a minimal number of tests can be conducted, with n=m. If one drug dosage is kept constant in the study, the number of tests n can be further reduced to $1+2(N-1)+((N-1)(N-2))/2$, for N>1.

In some embodiments, an experimental design methodology can be used to guide the selection of drug doses for respective in vitro or in vivo tests. In connection with the experimental design methodology, possible doses can be narrowed down into a few discrete levels.

Once tests are designed and conducted, experimental results of the tests (e.g., in terms of efficacies $E^k$) are then fitted into a model by using any suitable multi-dimensional fitting, such as regression analysis. Based on the fitting performance between the experimental results and the model, additional tests can be conducted to improve the accuracy of the model. Once the model with a desired accuracy is achieved, optimized combinations of input parameters of the system can be identified by using any suitable extrema locating technique, such as by locating global or local maxima in a response surface.

Taking the case of the quadratic model of drug efficacy E, for example, optimized doses can be identified once the constants $E_0$, and $a_i$ and $a_{ij}$ are derived through multi-dimensional fitting:

$$E_{max} = E_0 + \sum_i a_i \hat{C}_i + \sum_{i,j} a_{ij} \hat{C}_i \hat{C}_j$$

where $\{\hat{C}_i\}$ is an optimized dose of an $i^{th}$ drug from the pool of N total drugs.

In the case of a relatively large pool of drugs being evaluated (e.g., N≥10, 100, or even 1,000 or more), optimized sub-combinations of drugs can be identified to facilitate subsequent in vivo tests or clinical trials. For example, in the case of a pool of 6 total drugs, all optimized sub-combinations of 3 drugs from the pool of drugs can be identified, by setting doses of 3 drugs in the pool to zero to effectively reduce a 6-dimensional system to a 3-dimensional system, and locating maxima with respect to the 3 remaining dimensions. In this example of the pool of 6 drugs, a total of 20 different optimized sub-combinations of 3 drugs can be identified. Also, still in the case of the pool of 6 drugs, all optimized sub-combinations of 4 drugs from the pool of drugs can be identified, by setting dosages of 2 drugs in the pool to zero to effectively reduce the 6-dimensional system to a 4-dimensional system, and locating maxima with respect to the 4 remaining dimensions. In this example of the pool of 6 drugs, a total of 15 different optimized sub-combinations of 4 drugs can be identified. Thus, by conducting as few as 28 in vitro tests for the pool of 6 drugs, 35 (=20+15) optimized sub-combinations of 3 and 4 drugs can be identified as candidates for in vivo tests or clinical trials. In other embodiments, in vitro tests can be conducted to identify all optimized sub-combinations, and then a subset that is most suitable can be selected for animal tests. A similar procedure can be conducted in moving from animal tests to clinical trials.

Once a model with a desired accuracy is achieved for some embodiments, the significance of each input parameter and its synergistic effect with other input parameters can be identified. Non-significant input parameters that have little or no impact in affecting a state of a complex system can be dropped or omitted from an initial pool of input parameters, thereby effectively converting an initial multi-dimensional system to a refined system with a lower dimensionality. Taking the case of the quadratic model of drug efficacy E, for example, non-significant drugs can be identified as having low values of the constants $a_i$ and $a_{ij}$, and can be dropped from an initial pool of drugs for subsequent evaluation.

v. Definitions

As used herein, the singular terms "a," "an," and "the" include plural referents unless the context clearly dictates otherwise. Thus, for example, reference to an object can include multiple objects unless the context clearly dictates otherwise.

As used herein, the terms "substantially" and "about" are used to describe and account for small variations. When used in conjunction with an event or circumstance, the terms can refer to instances in which the event or circumstance occurs precisely as well as instances in which the event or circumstance occurs to a close approximation. When used in conjunction with a numerical value, the terms can refer to a range of variation of less than or equal to ±10% of that numerical value, such as less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%.

Additionally, amounts, ratios, and other numerical values are sometimes presented herein in a range format. It is to be understood that such range format is used for convenience and brevity and should be understood flexibly to include numerical values explicitly specified as limits of a range, but also to include all individual numerical values or sub-ranges encompassed within that range as if each numerical value and sub-range is explicitly specified. For example, a ratio in the range of about 1 to about 200 should be understood to include the explicitly recited limits of about 1 and about 200, but also to include individual ratios such as about 2, about 3, and about 4, and sub-ranges such as about 10 to about 50, about 20 to about 100, and so forth.

In some embodiments, clofazimine (CLZ) corresponds to N,5-bis(4-chlorophenyl)-3-(propan-2-ylimino)-3,5-dihydro-phenazin-2-amine, and is represented by the following structure, or a pharmaceutically acceptable salt thereof:

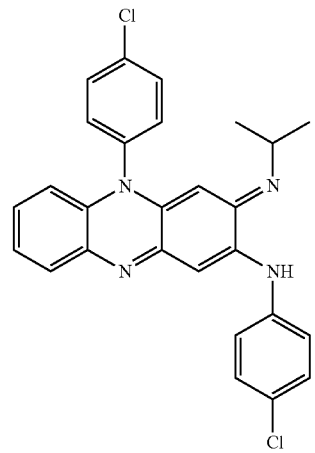 [SMILES: CC(C)/N=c1\cc2n(-c3ccc(Cl)cc3)c3ccccc3nc-2cc1Nc1ccc(Cl)cc1]

In some embodiments, ethambutol (EMB) corresponds to (2S,2'S)-2,2'-(Ethane-1,2-diyldiimino)dibutan-1-ol, and is represented by the following structure, or a pharmaceutically acceptable salt thereof:

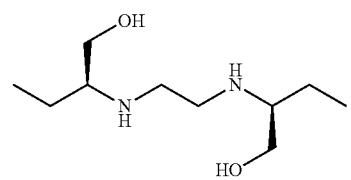

In some embodiments, 4-aminosalicyclic acid (PAS) corresponds to 4-amino-2-hydroxy-benzoic acid, and is represented by the following structure, or a pharmaceutically acceptable salt thereof:

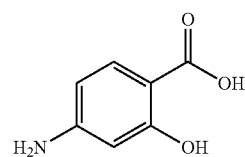

In some embodiments, bedaquiline (TMC207) corresponds to (1R,2S)-1-(6-Bromo-2-methoxy-3-quinolyl)-4-dimethylamino-2-(1-naphthyl)-1-phenyl-butan-2-ol, and is represented by the following structure, or a pharmaceutically acceptable salt thereof:

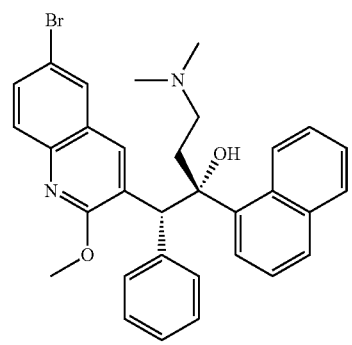 [SMILES: COc1nc2ccc(Br)cc2cc1[C@@H](c1ccccc1)[C@@](O)(CCN(C)C)c1cccc2ccccc12]

In some embodiments, rifampin (RIF) is represented by the following structure, or a pharmaceutically acceptable salt thereof:

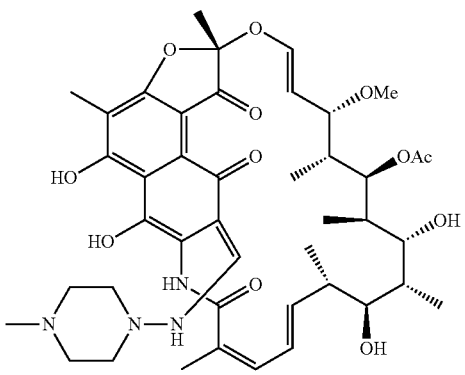

In some embodiments, pyrazinamide (PZA) corresponds to pyrazine-2-carboxamide, and is represented by the following structure, or a pharmaceutically acceptable salt thereof:

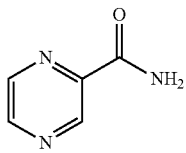

In some embodiments, prothionamide (PRO) corresponds to 2-propylpyridine-4-carbothioamide, and is represented by the following structure, or a pharmaceutically acceptable salt thereof:

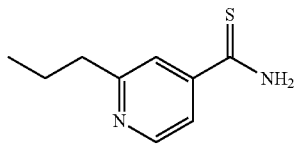

In some embodiments, SQ09 corresponds to N-Adamantan-2-yl-N'-((E)-3,7-dimethyl-octa-2,6-dienyl)-ethane-1,2-diamine, and is represented by the following structure, or a pharmaceutically acceptable salt thereof:

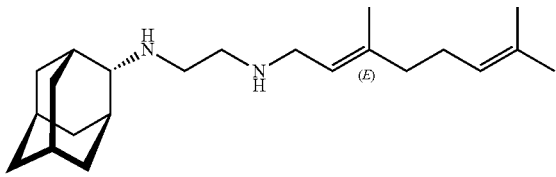

In some embodiments, pretomanid (PA824) corresponds to (6S)-2-nitro-6-{[4-(trifluoromethoxy)benzyl]oxy}-6,7-dihydro-5H-imidazo[2,1-b][1,3]oxazine, and is represented by the following structure, or a pharmaceutically acceptable salt thereof:

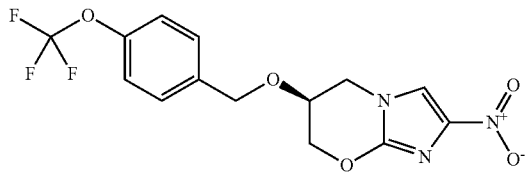 [SMILES: O=[N+]([O-])c1cn2c(n1)OC[C@@H](OCc1ccc(OC(F)(F)F)cc1)C2]

Those of skill in the art will appreciate that compounds of the invention may exhibit the phenomena of tautomerism, conformational isomerism, geometric isomerism and/or optical isomerism. As the formula drawings within the specification and claims can represent only one of the possible tautomeric, conformational isomeric, optical isomeric or geometric isomeric forms, it should be understood that the invention encompasses any tautomeric, conformational isomeric, optical isomeric and/or geometric isomeric forms of the compounds having one or more of the utilities described herein, as well as mixtures of these various different forms.

"Tautomers" refers to isomeric forms of a compound that are in equilibrium with each other. The concentrations of the isomeric forms will depend on the environment the compound is found in and may be different depending upon, for example, whether the compound is a solid or is in an organic or aqueous solution. For example, in aqueous solution, pyrazoles may exhibit the following isomeric forms, which are referred to as tautomers of each other:

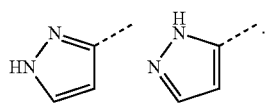

As readily understood by one skilled in the art, a wide variety of functional groups and other structures may exhibit tautomerism, and all tautomers of compounds as described herein are within the scope of the present invention.

Stereoisomers of compounds, also known as "optical isomers," include all diastereomeric, and racemic forms of a structure, unless the specific stereochemistry is expressly indicated. Thus, compounds used in the present invention include enriched or resolved optical isomers at any or all asymmetric atoms as are apparent from the depictions. Both racemic and diastereomeric mixtures, as well as the individual optical isomers can be isolated or synthesized so as to be substantially free of their enantiomeric or diastereomeric partners, and these are all within the scope of the invention.

By "pharmaceutically acceptable" is meant a material that is not biologically or otherwise undesirable, i.e., the material may be incorporated into a pharmaceutical composition administered to a patient without causing any undesirable biological effects or interacting in a deleterious manner with any of the other components of the composition in which it is contained. When the term "pharmaceutically acceptable" is used to refer to a pharmaceutical carrier or excipient, it is implied that the carrier or excipient has met the required standards of toxicological and manufacturing testing or that it is included on the Inactive Ingredient Guide prepared by the U.S. and Drug administration.

By "patient" is meant any animal for which treatment is desirable. Patients may be mammals, and typically, as used herein, a patient is a human individual.

The term "pharmaceutically acceptable salt," as used herein, represents salts or zwitterionic forms of the compounds of the present invention which are water or oil-soluble or dispersible; which are suitable for treatment of diseases without undue toxicity, irritation, and allergic-response; which are commensurate with a reasonable benefit/risk ratio; and which are effective for their intended use. The salts can be prepared during the final isolation and purification of the compounds or separately by reacting the appropriate compound in the form of the free base with a suitable acid. Representative acid addition salts include acetate, adipate, alginate, L-ascorbate, aspartate, benzoate, benzenesulfonate (besylate), bisulfate, butyrate, camphorate, camphorsulfonate, citrate, digluconate, formate, fumarate, gentisate, glutarate, glycerophosphate, glycolate, hemisulfate, heptanoate, hexanoate, hippurate, hydrochloride, hydrobromide, hydroiodide, 2-hydroxyethansulfonate (isethionate), lactate, maleate, malonate, DL-mandelate, mesitylenesulfonate, methanesulfonate, naphthylenesulfonate, nicotinate, 2-naphthalenesulfonate, oxalate, pamoate, pectinate, persulfate, 3-phenylproprionate, phosphonate, picrate, pivalate, propionate, pyroglutamate, succinate, sulfonate, tartrate, L-tartrate, trichloroacetate, trifluoroacetate, phosphate, glutamate, bicarbonate, para-toluenesulfonate (p-tosylate), and undecanoate. Also, basic groups in the compounds of the present invention can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form pharmaceutically acceptable addition salts include inorganic acids such as hydrochloric, hydrobromic, sulfuric, and phosphoric, and organic acids such as oxalic, maleic, succinic, and citric. Salts can also be formed by coordination of the compounds with an alkali metal or alkaline earth ion. Hence, the present invention contemplates sodium, potassium, magnesium, and calcium salts of the compounds of the compounds of the present invention and the like.

The term "solvates" is used in its broadest sense. For example, the term solvates includes hydrates formed when a compound of the present invention contains one or more bound water molecules.

Certain ranges are presented herein with numerical values being preceded by the term "about". The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

While the disclosure has been described with reference to the specific embodiments thereof, it should be understood by those skilled in the art that various changes may be made and equivalents may be substituted without departing from the true spirit and scope of the disclosure as defined by the appended claim(s). In addition, many modifications may be made to adapt a particular situation, material, composition of matter, method, operation or operations, to the objective, spirit and scope of the disclosure. All such modifications are intended to be within the scope of the claim(s) appended hereto. In particular, while certain methods may have been described with reference to particular operations performed in a particular order, it will be understood that these operations may be combined, sub-divided, or re-ordered to form an equivalent method without departing from the teachings of the disclosure. Accordingly, unless specifically indicated herein, the order and grouping of the operations is not a limitation of the disclosure.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

vi. Working Examples

The present technology is further illustrated by the following examples, which should not be construed as limiting in any way.

Inhibition Assay: In Vitro Macrophage Assay Testing the Efficacy of TB Drug Combinations by Quantifying Fluorescence Preparation of *M. tuberculosis* Bacteria These experiments utilized an *M. tuberculosis* Erdman inducible GFPuv strain (Mtb-iGFP) to infect human macrophages. This strain is induced to fluoresce when incubated with the inducer IPTG. To prepare the infecting inoculum, a glycerol stock of this strain was cultured on 7H11 agar plates containing hygromycin (about 50 µg/ml) and kanamycin (about 15 and incubated the cultures at about 37° C., about 5% $CO_2$-95% air for 10 days. Bacterial lawns were scraped from the agar plates into RPMI-1640 supplemented with about 20 mM HEPES. Bacterial aggregates were dispersed by sonication of the bacterial suspension in a water bath sonicator for 8 periods of about 15 seconds, with cooling of the suspension in an ice bath for about 5 seconds in between sonications. Residual aggregates were removed by centrifugation at about 200 g for about 10 min at about 4° C. The pellet of aggregated bacteria was discarded and the supernate suspension centrifuged again under the same conditions, and the process repeated for a total of five times. Optical density of the final suspension was measured in a spectrophotometer at about 540 nm. Bacterial numbers in the final suspension was determined according to the formula of $OD_{540}$ of $0.1=2\times10^7$ bacteria/ml. The bacteria ($OD_{540}$ of 0.2) were opsonized in RPMI with about 10% human serum type AB at about 37° C. for about 10 min, diluted 20-fold, and used to infect macrophages.

Preparation of Human Macrophages

Human monocytic cell line, THP-1, was grown in RPMI-1640 supplemented with about 2 mM glutamine, about 10% heat-inactivated fetal bovine serum, and penicillin-streptomycin (about 100 U/ml and about 100 µg/ml, respectively). Prior to use in infection experiments, the THP-1 cells were spun down by centrifugation at about 200 g for about 10 min at room temperature, re-suspended in RPMI-1640 supplemented with about 2 mM glutamine, about 10% heat-inactivated fetal bovine serum and phorbol 12-myristate 13-acetate (about 100 nM), and seeded in Matrical 96-well glass bottom plates at a density of about $1 \times 10^5$ cells/200 µl/well for 3 days at about 37° C., about 5% $CO_2$-95% air atmosphere.

Testing TB Drug Combinations

Monolayers of phorbol 12-myristate 13-acetate differentiated THP-1 cells were infected for about 90 min with Mtb-iGFP at a ratio of about 10:1, washed with RPMI, and incubated in medium with about 1 mM IPTG and experimental TB drug combinations. Included in each 96-well plate were: wells not infected with tuberculosis (No Infection Control); wells to which the inducer IPTG were not added (No IPTG Control); and wells to which TB drugs were not added (No Drug Control). All conditions were in triplicate with randomized well positions. The cultures were incubated for 4 days before fixing for one hour in about 4% paraformaldehyde in Dulbecco's Phosphate Buffered Saline (PBS). Cell nuclei were stained for about 10 min with about 1 µg/ml Hoechst 33342 in PBS containing about 0.1% Tween 20. Monolayers were washed twice with PBS and imaged with an ImageXpress (Molecular Devices) high throughput epifluorescence microscope using a 10× objective lens. Three GFP and Hoechst epifluorescence images were acquired from non-overlapping regions of each well using FITC and DAPI filter cubes, respectively. Automated image analysis was done using the Granularity and Count Nuclei modules of MetaXpress (Molecular Devices) software to quantitate the integrated GFP fluorescence intensity and the number of macrophage nuclei, respectively, for each area imaged.

An example of a dose-response assay for moxifloxacin is shown in FIG. 1.

Figure 2A:
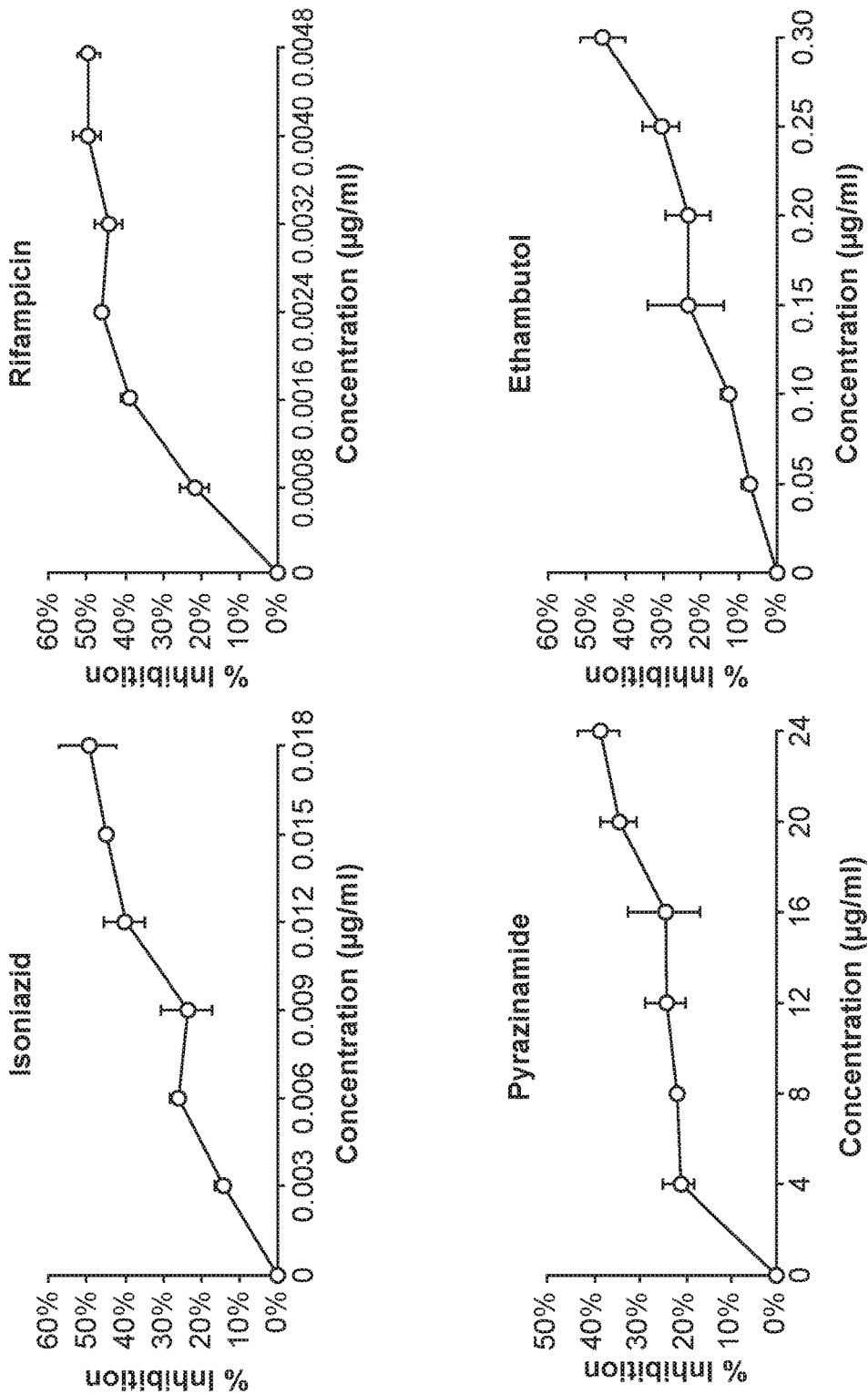
FIG. 2A shows Dose Response of the Standard Regimen.
Figure 2B:
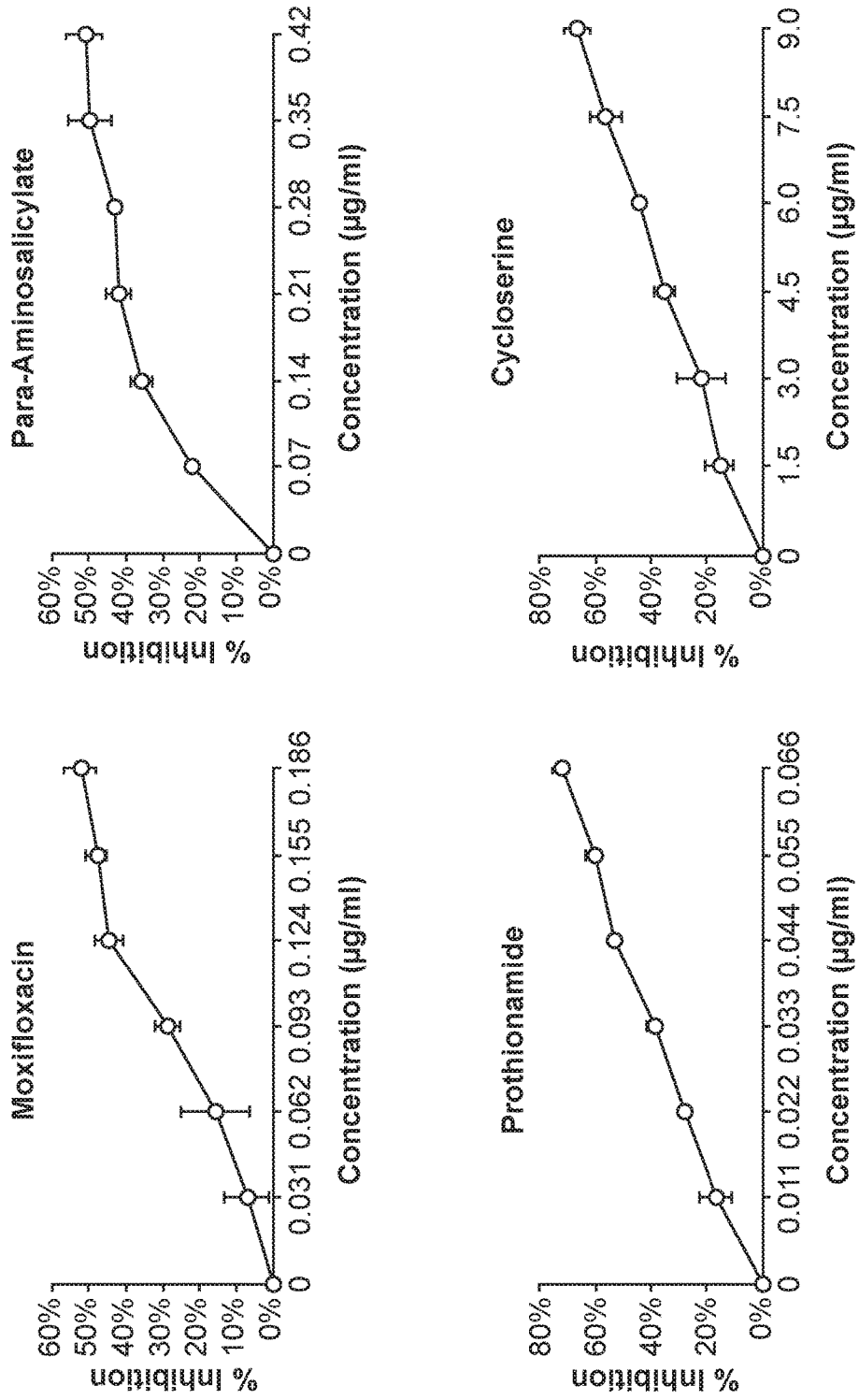
FIG. 2B shows Dose Response of the Second Line TB Drugs.
Figure 2C:
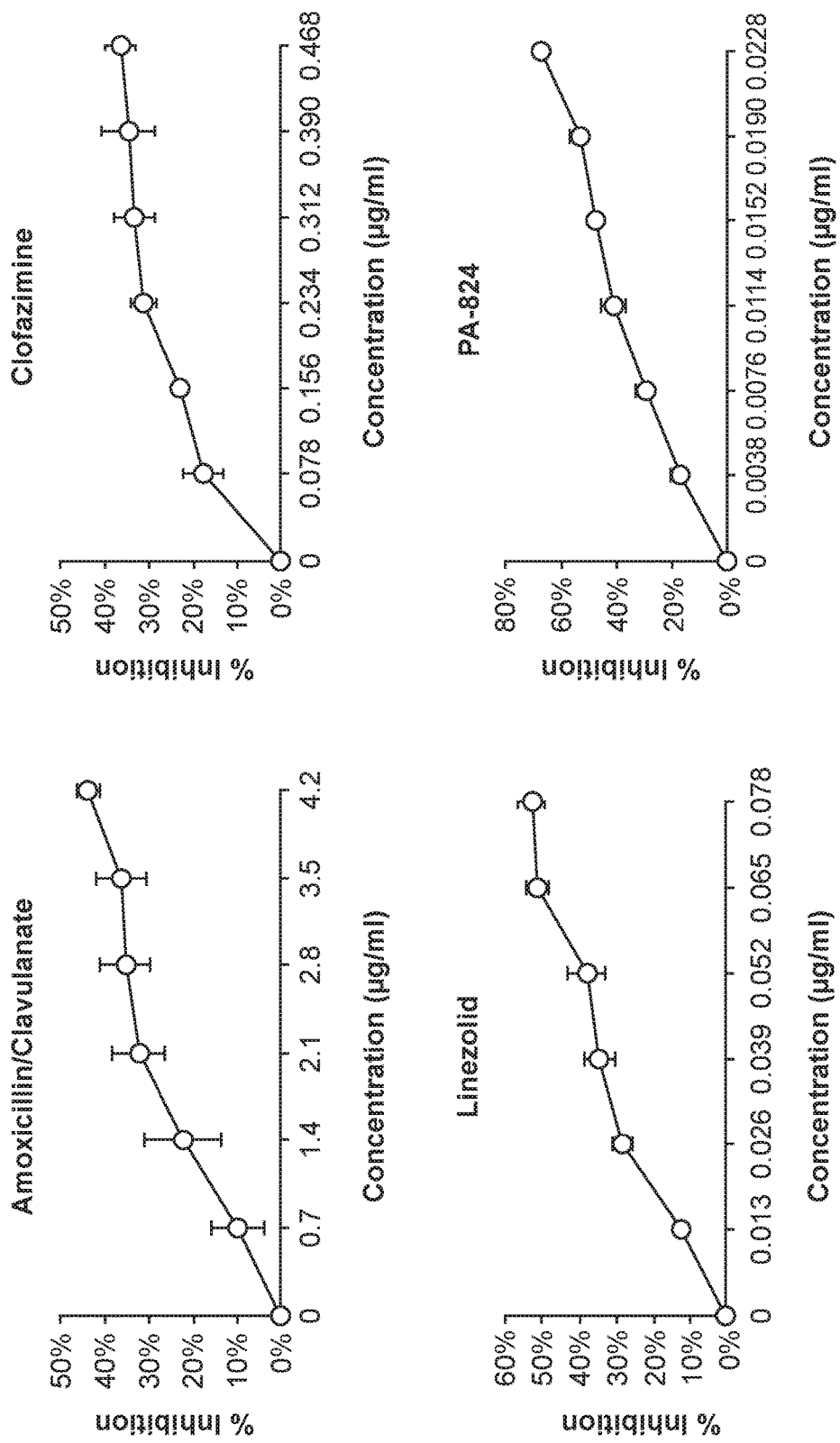
FIG. 2C shows Dose Response of the Experimental TB Drugs.
Figure 2C:
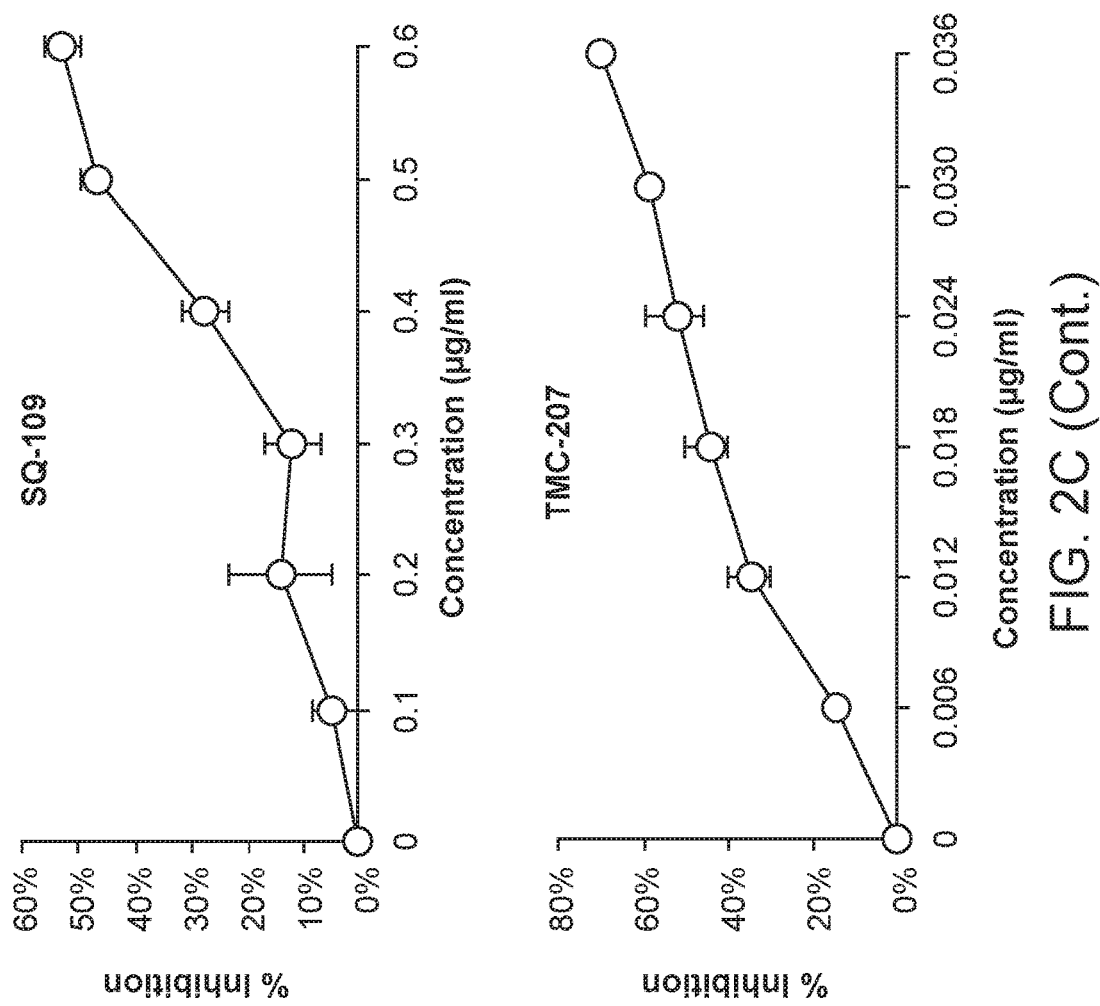

Dose-response curves for all 14 drugs, including the Standard Regimen drugs, Second-line Drugs, and Experimental TB drugs are shown in FIGS. 2A-2C.

Figure 3:
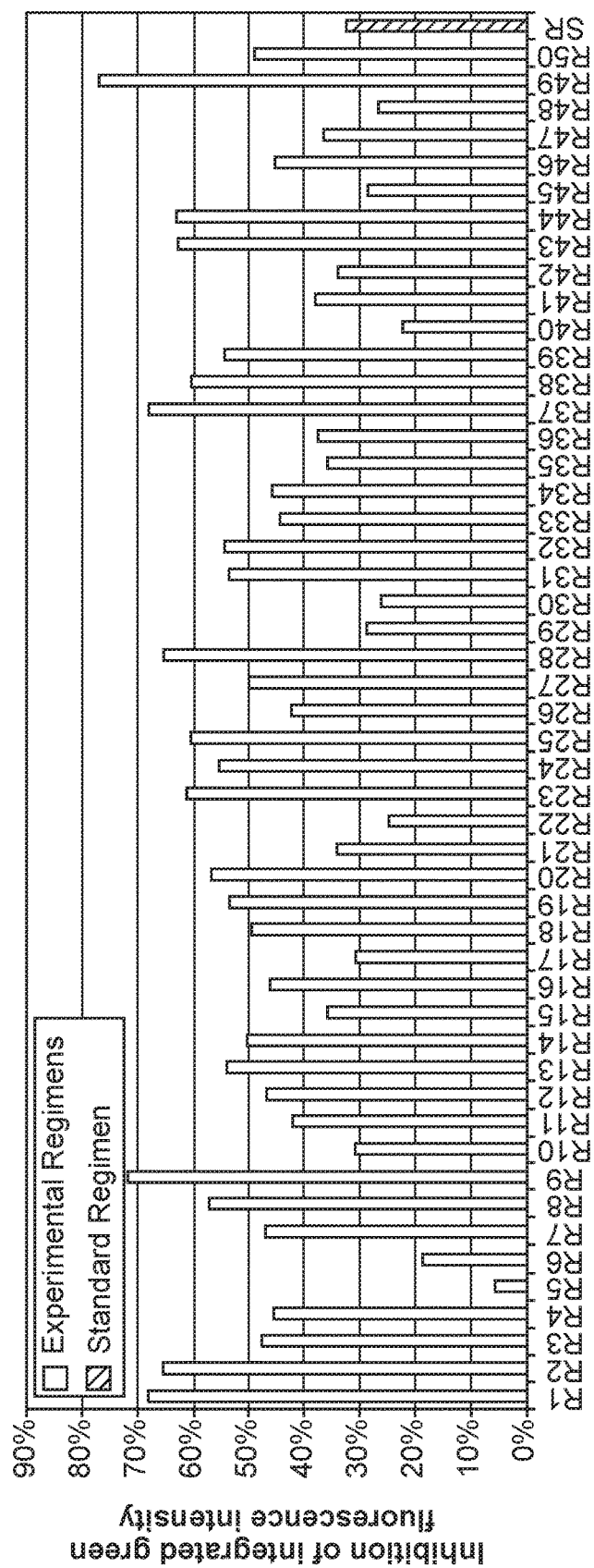
FIG. 3 shows inhibition of *M. tuberculosis* in in vitro inhibition assay testing combinations of 5 TB drugs vs. Standard Regimen.

The results of the final inhibition assay are shown in FIG. 3. In FIG. 3, inhibition of M. tuberculosis in in vitro inhibition assay testing combinations of 5 TB drugs vs. Standard Regimen. Final Inhibition assay. Fifty regimens of TB drugs and the Standard Regimen were tested in the assay for inhibition of M. tuberculosis growth, as assayed by fluorescence measurement. The percent inhibition of M. tuberculosis fluorescence is shown for each combination. Many combinations show greater inhibition than the Standard Regimen.

(II) Killing Assay: In Vitro Macrophage Assay Testing the Efficacy of TB Drug Combinations by Quantifying Colony-Forming Units (CFU)

Bacteria

M. tuberculosis Erdman strain was used to infect macrophages in these studies. M. tuberculosis from a glycerol stock was spread on 7H11 agar plates and incubated at about 37° C., about 5% $CO_2$-95% air for 10 days. The bacteria were prepared as described in the section above for use in infection of human macrophages.

Macrophage

Prepared as described above.

Testing TB Drug Combinations

Monolayers of phorbol 12-myristate 13-acetate differentiated THP-1 cells were infected for about 90 min with M. tuberculosis at a ratio of about 10:1, washed with RPMI, and incubated in medium with no drug (No drug control), the Standard Regimen (INH, RIF, EMB, and PZA), or Experimental TB Drug Regimens at about 37° C., about 5% $CO_2$-95% air atmosphere. The Standard Regimen and Experimental TB Drugs were administered at dosages of 1×, 4×, and 16×, where the 1× drug concentration was the 20% inhibition dose in the fluorescence assay. M. tuberculosis were harvested for enumeration of CFU from the No drug control well at about 90 min, 1 day and 3 days to establish the amount of bacterial growth, and M. tuberculosis were harvested from all drug-treated wells at 1 day and 3 days to assess drug efficacy. To enumerate the number of live M. tuberculosis in wells, the infected macrophages were lysed with about 0.1% SDS for about 10 seconds, serial diluted the lysate, and plated the dilutions on 7H11-0.4% charcoal agar. The plates were incubated at about 37° C., about 5% $CO_2$-95% air atmosphere for 4 weeks, after which the number of CFU of M. tuberculosis on each plate was counted.

Results of the in vitro killing assay are shown below in FIGS. 4 and 5.

Figure 4A:
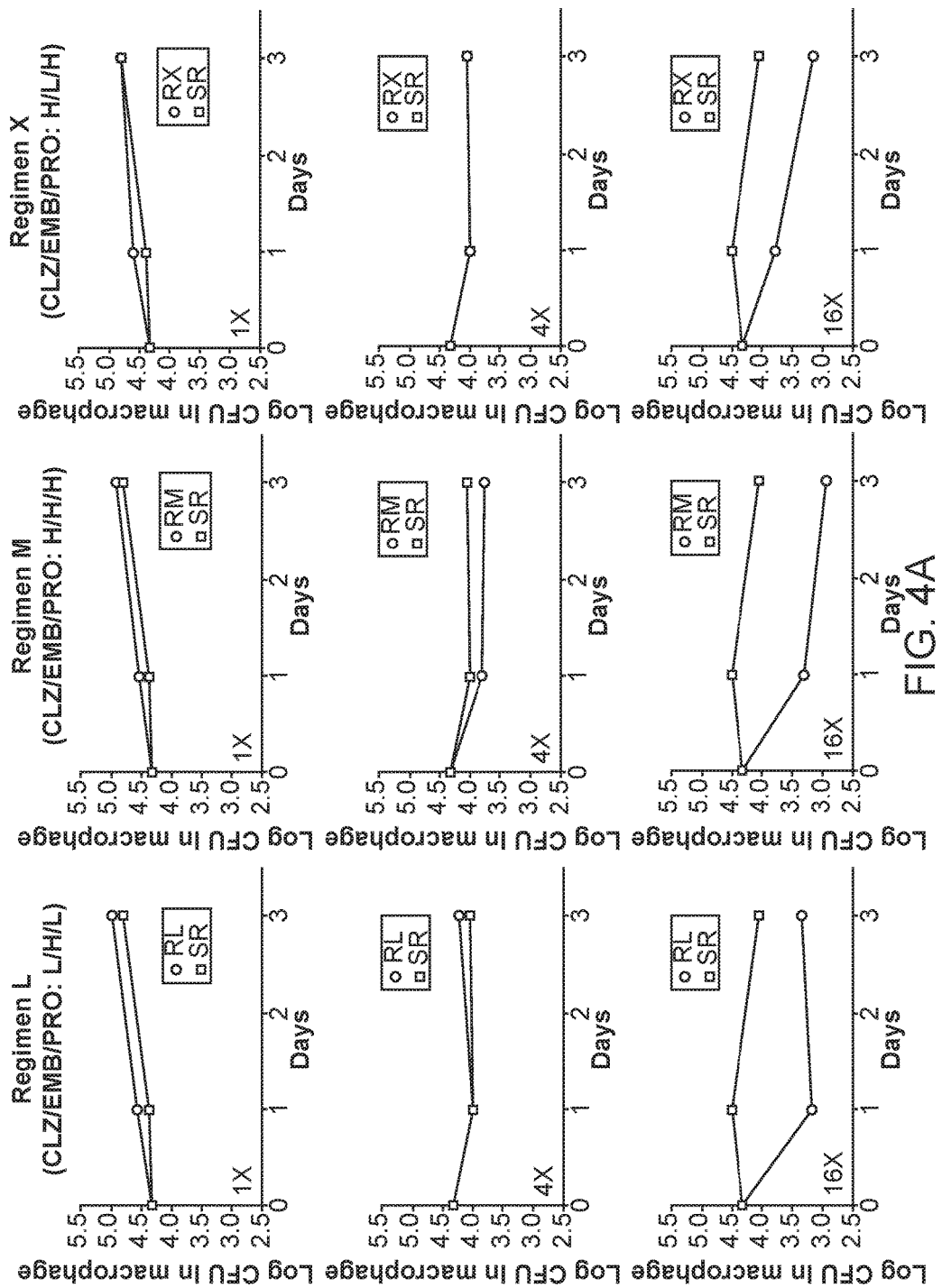
FIG. 4A shows 3-Drug Experimental Regimens.
Figure 4A:
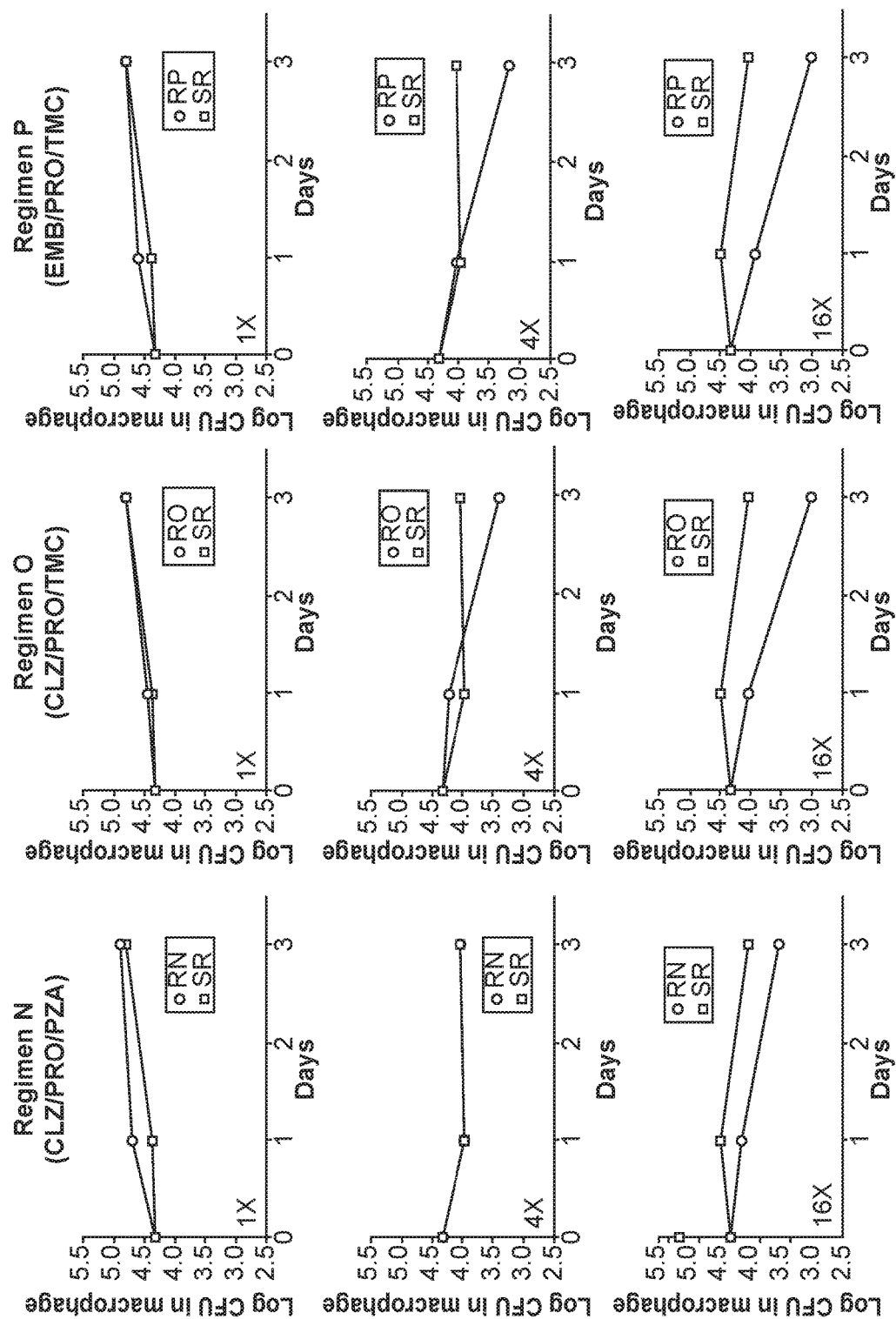
Figure 4B:
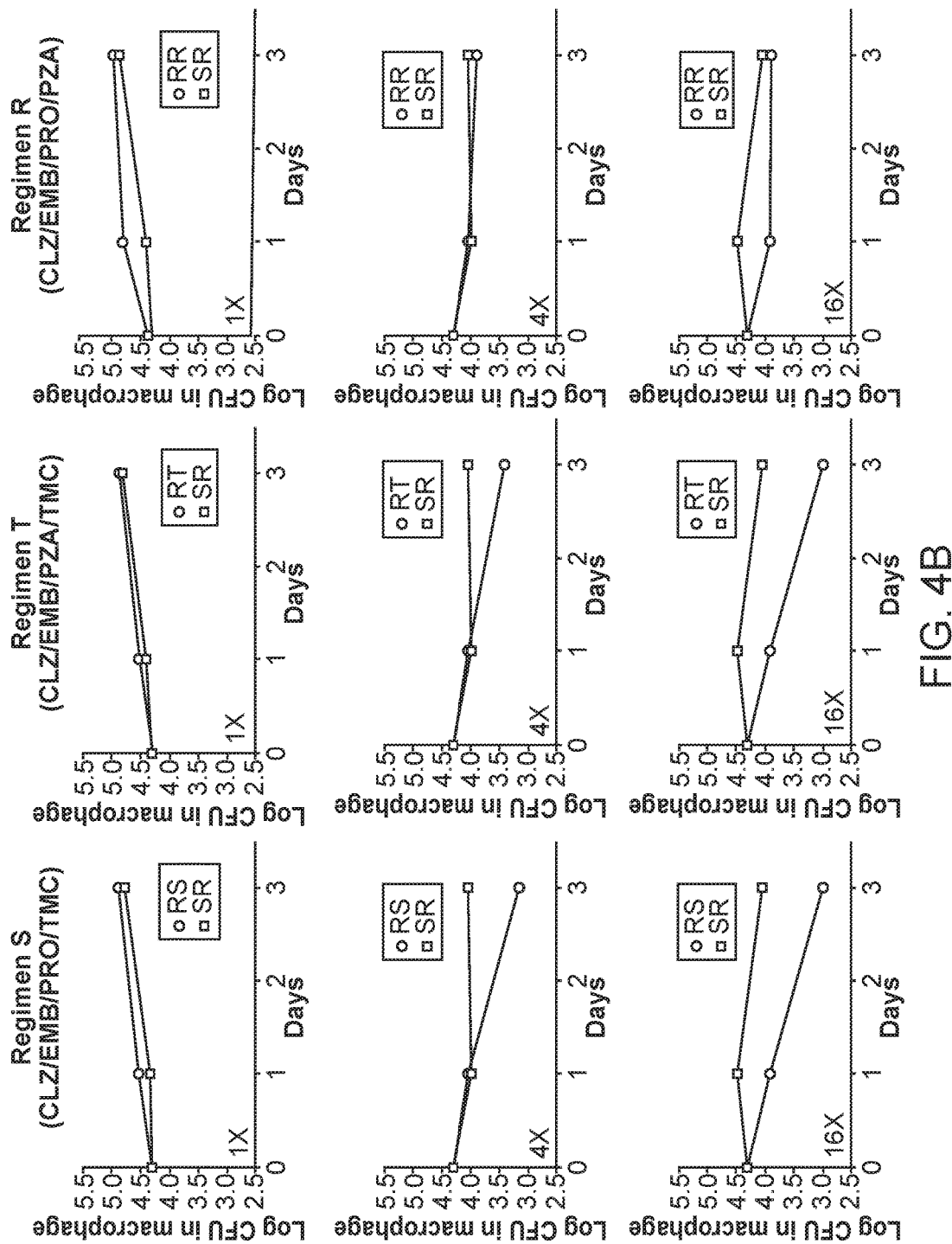
FIG. 4B shows 4-Drug Experimental Regimens.
Figure 4B:
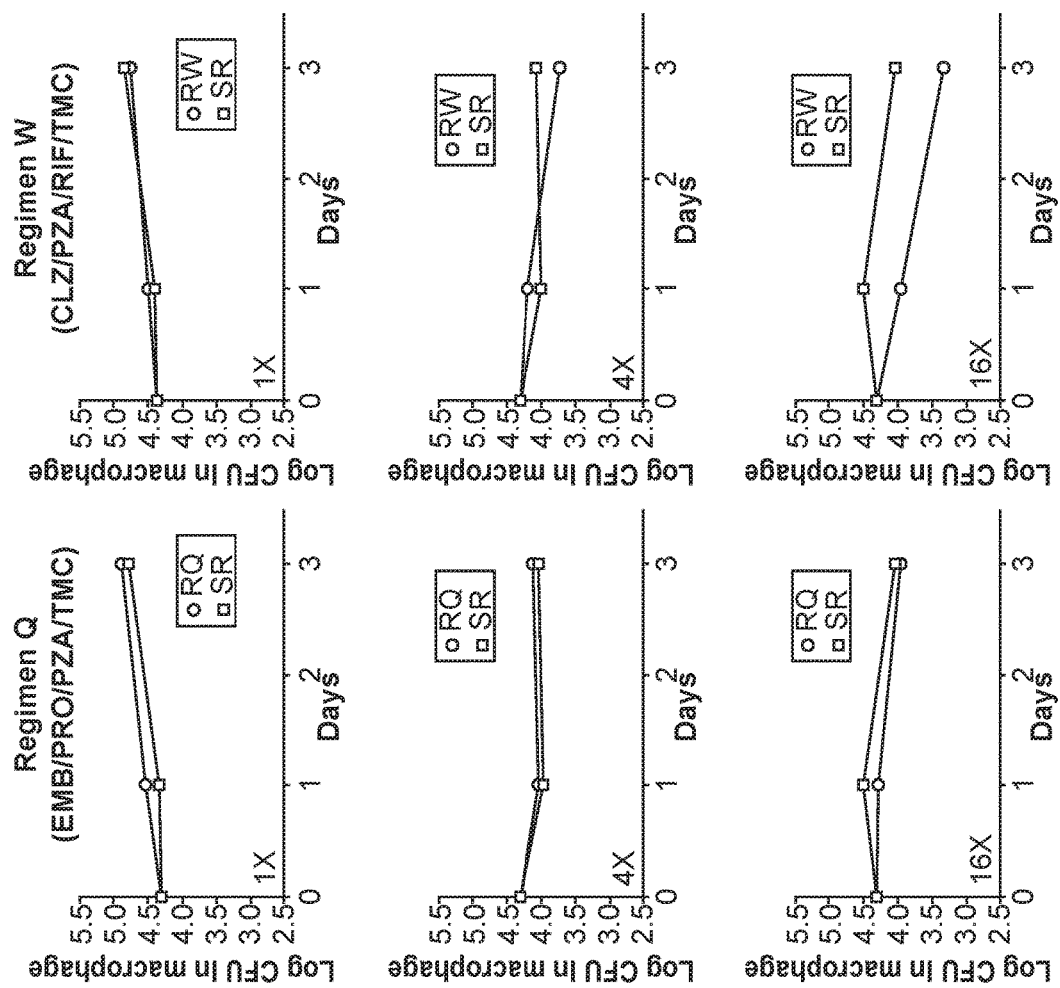

FIG. 4A shows 3-Drug Experimental Regimens. FIG. 4B shows 4-Drug Experimental Regimens.

Figure 11:
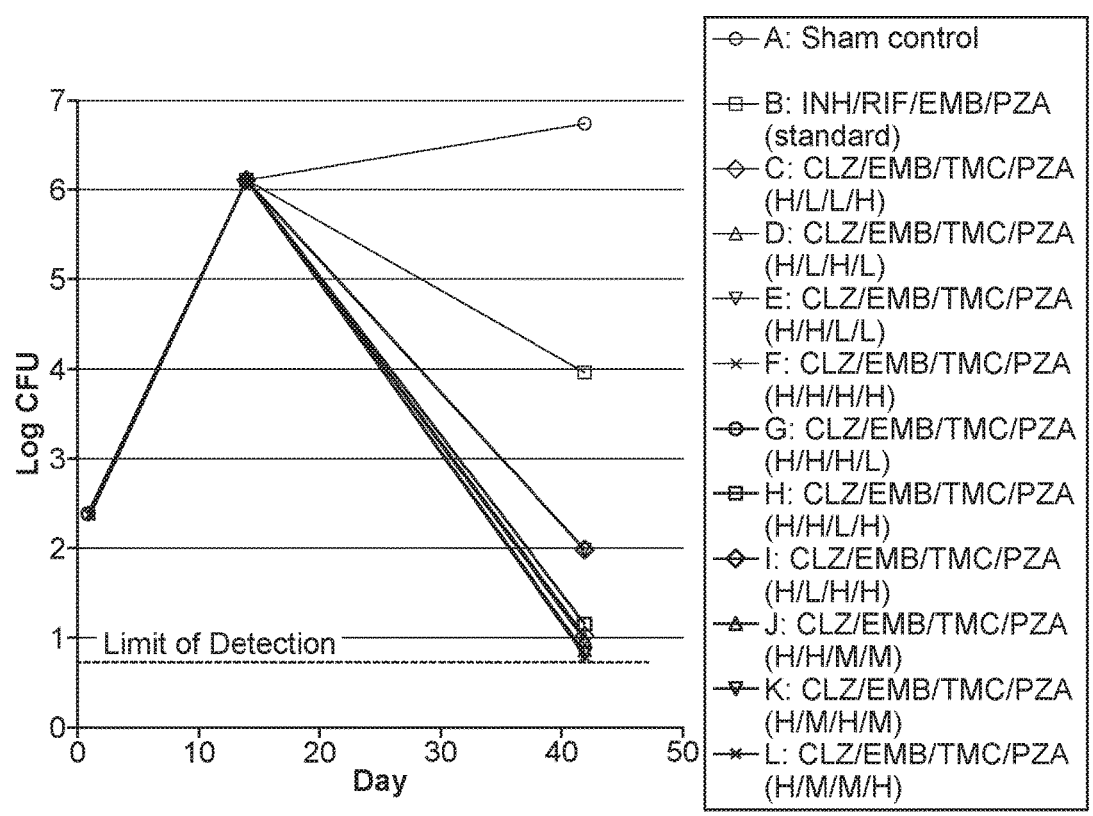
FIG. 11 shows the data at the start of the experiment (Day 0), 14 days after challenge (Day 14) and 28 days after the start of treatment (Day 42). *M. tuberculosis* CFU per lung from mice in groups A-L over the course of infection and treatment. Mice were infected with *M. tuberculosis* Erdman by aerosol (Day 0), treated starting 14 days after challenge for 4 weeks (Days 14-39) and euthanized 3 days after the end of treatment (Day 42) to determine bacterial burden in the lung. Mice in groups C-L were treated with FSC Regimen II, a drug combination consisting CLZ, EMB, TMC, and PZA with the individual drugs at high (H), middle (M) or low (L) dose.

In FIG. 11, it is shown the killing of M. tuberculosis in in vitro killing assay. The various Experimental Drug Regimens A and M-W (RA, RM-RW, as indicated) are plotted against the Standard Regimen (SR) at 1×, 4×, and 16× concentrations, as indicated. Experimental Drug Regimens L and X (RL, RX, as indicated) are also plotted against the Standard Regimen (SR) at 1×, 4×, and 16× concentrations but with Regimen L, the doses of CLZ and PRO were halved C indicates half of the regular dose be it 1×, 4× or 16×; H is the regular dose) and with Regimen X, the dose of EMB was halved. (Again, "L" indicates half of the regular dose be it 1×, 4× or 16×). The Experimental Regimens containing 3 drugs are shown in FIG. 11A, and Experimental Regimens containing 4 drugs are shown in FIG. 11B. The Standard. Regimen was always 4 drugs. Especially at the 16× concentrations, many of the Experimental Drug regimens are superior to the Standard Regimen.

Figure 5A:
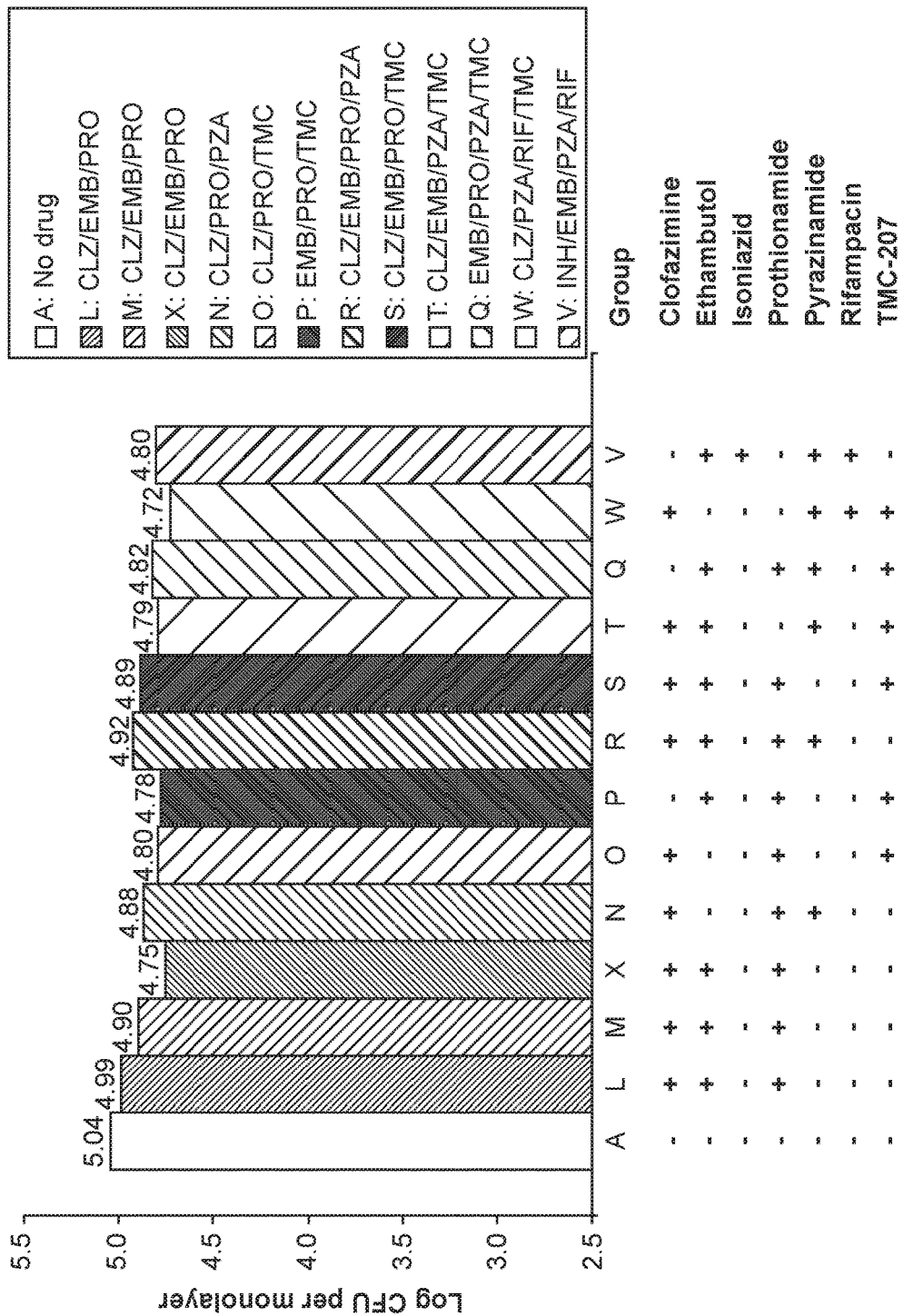
FIGS. 5A, 5B and 5C show 1× Drug Concentrations, 4× Drug Concentrations, and 16× Drug Concentrations, respectively.
Figure 5B:
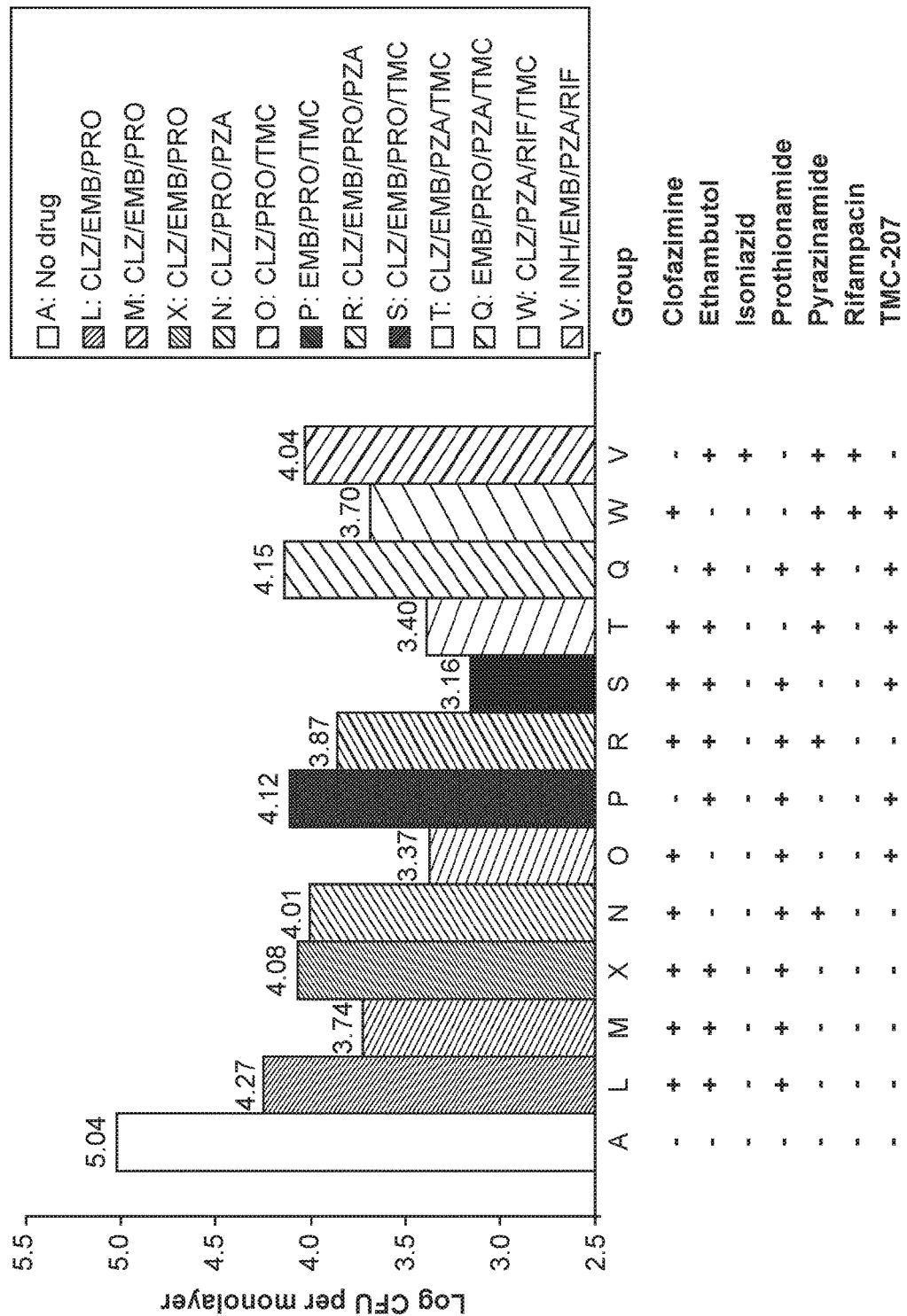
Figure 5C:
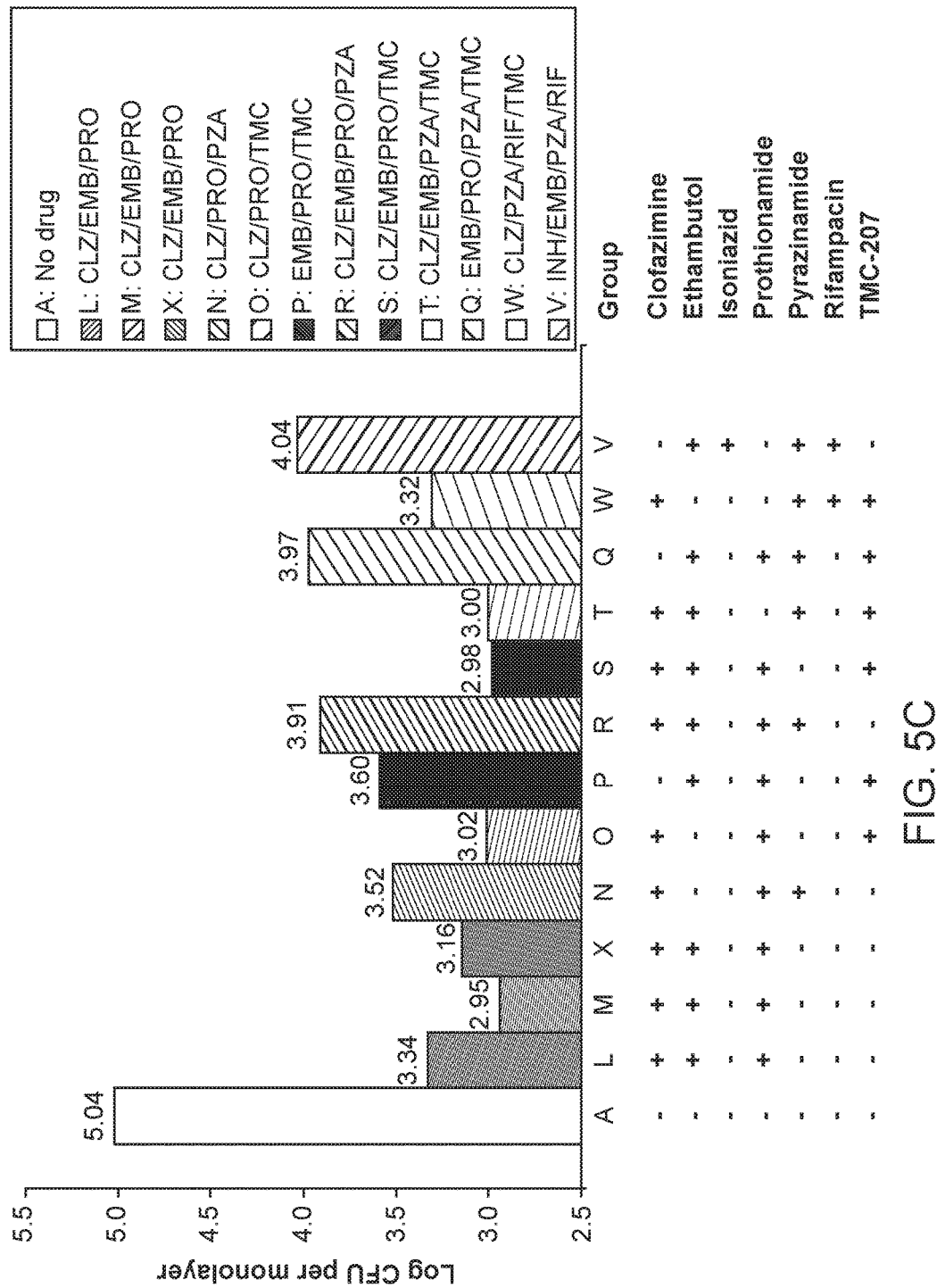
Figure 6:
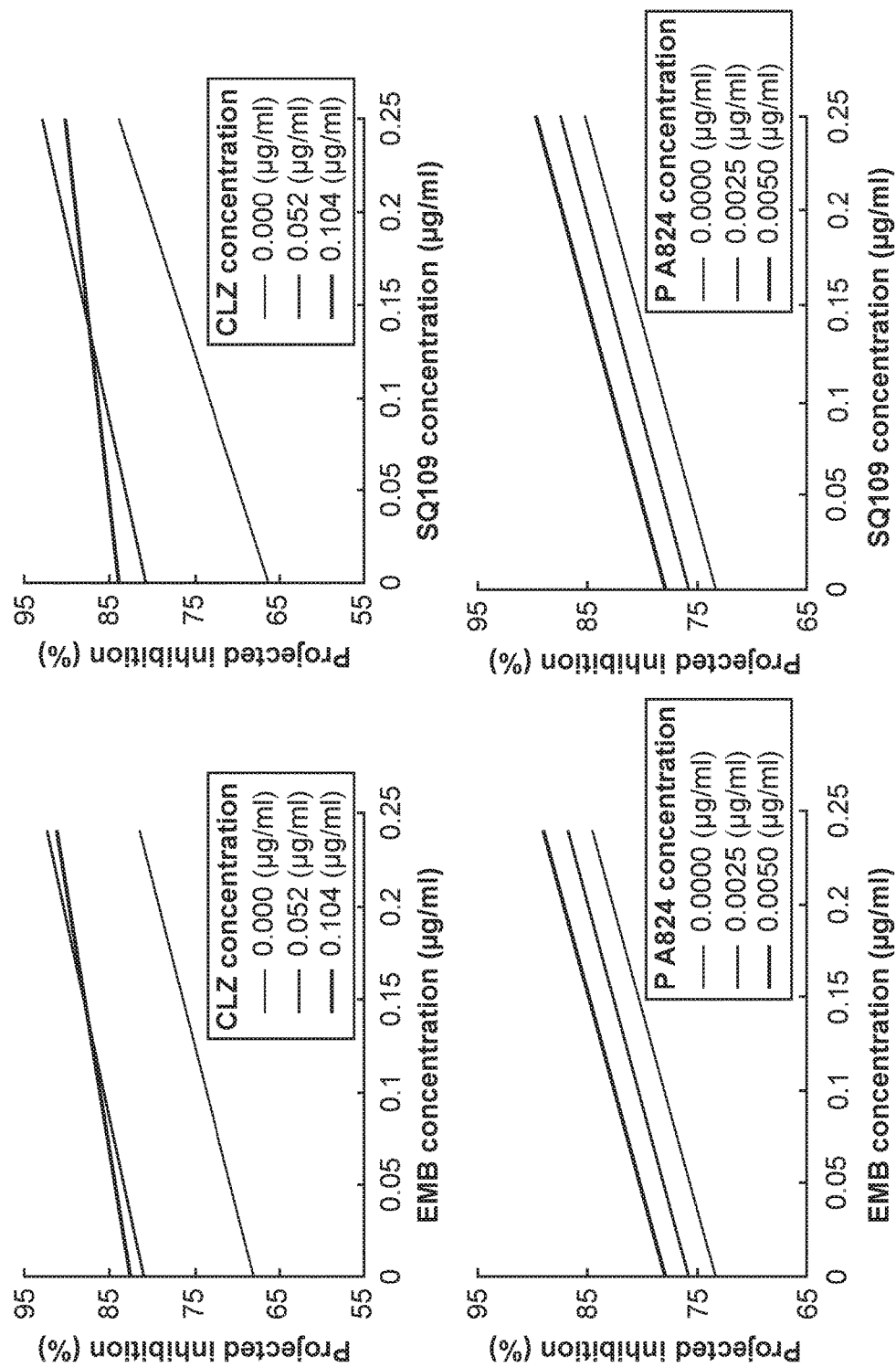
FIG. 6 shows similarities between EMB and SQ109.
Figure 6:
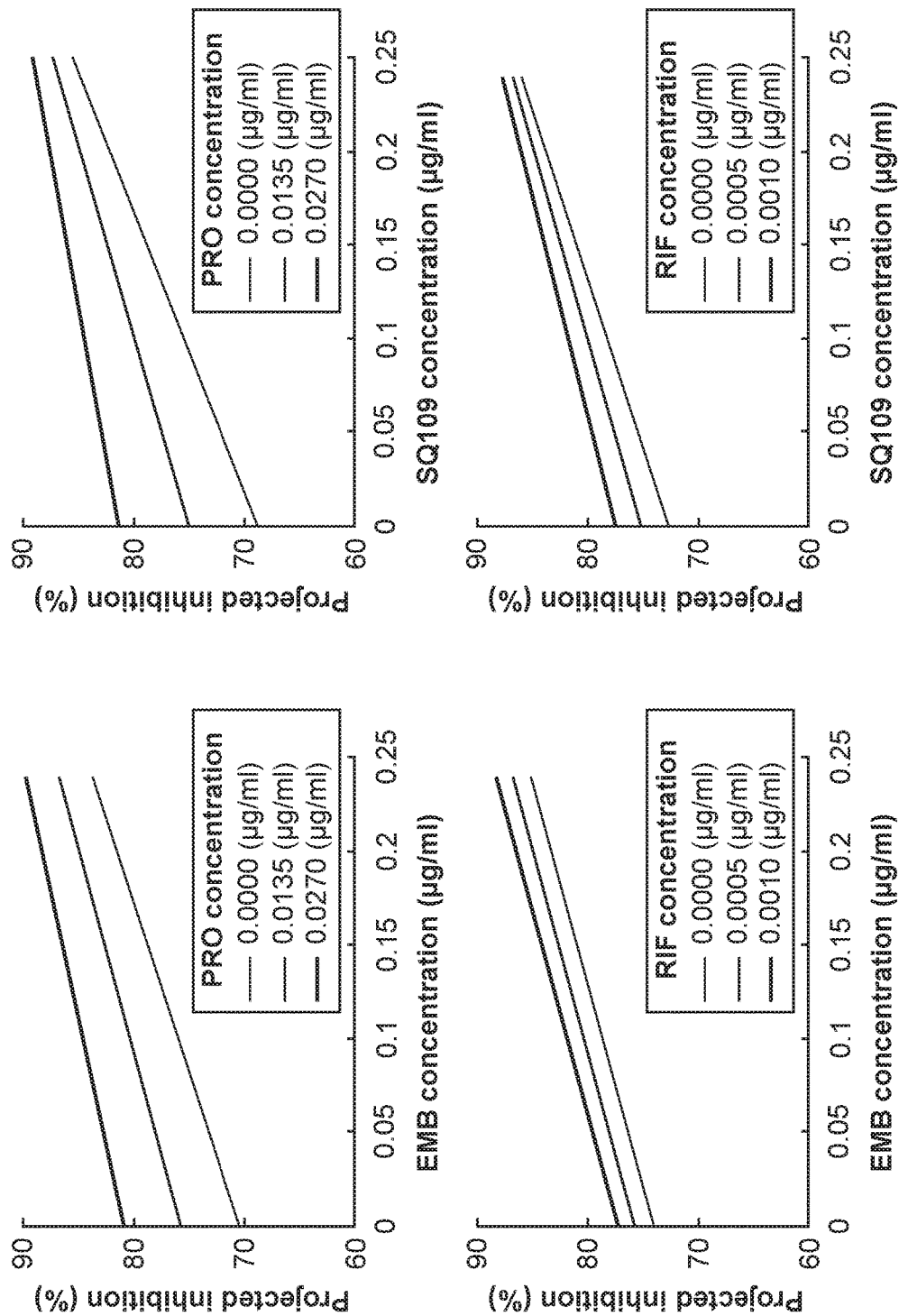

FIGS. 5A, 5B and 5C show 1× Drug Concentrations, 4× Drug Concentrations, and 16× Drug Concentrations, respectively. In FIGS. 5A-5C, the various Experimental Drug Regimens A and are plotted against the Standard Regimen (V) at 1×, 4×, and 16× concentrations, as indicated. Experimental Drug Regimens L and X are also plotted against the Standard Regimen (V) at 1×, 4×, and 16× concentrations but with Regimen L, the doses of CLZ and PRO were halved (half of the regular dose be it 1×, 4× or 16×) and with Regimen X, the dose of EMB was halved (half of the regular dose be it 1×, 4× or 16×). The 3-day CFU data from the in vitro killing assay in macrophages is presented. Data are the log CFU of M. tuberculosis/well for each of the regimens. The drugs comprising the regimens are listed to the right of the graphs and also indicated by a "+" sign below the bars. Especially at the 16× concentrations, many of the Experimental Drug regimens are superior to the Standard Regimen.

Efficacy of Drug Combinations in an In Vitro Intramacrophage Mtb-iGFP Model

Monolayers of differentiated THP-1 cells (from a human monocytic cell line) were infected for about 3 h with *M. tuberculosis*-iGFP (Mtb-iGFP) prior to incubating in medium with isopropyl β-D-1-thiogalactopyranoside (IPTG) and the experimental TB drug combinations. The drug combinations tested were determined by an orthogonal array central composite design (OACD) according to the FSC scheme. Monolayers were imaged with an ImageXpress (Molecular Devices) high throughput epifluorescence microscope, and the inhibition was calculated by the following equation:

$$\text{Inhibition} = 1 - \left( \frac{\text{Integrated } GFP \text{ Fluorescence Intensity per Nucleus of Treated Sample}}{\text{Integrated } GFP \text{ Fluorescence Intensity per Nucleus of Untreated Sample}} \right)$$

The results obtained were used to fit a quadratic model following the FSC scheme. Using this model, the following optimal drug-dose combinations are identified for TB:

TABLE 3

FSC-projected Inhibition of 3- and 4-drug combinations. Concentration for each drug is expressed in µg/ml.

| CLZ | EMB | PA824 | PAS | PRO | PZA | RIF | SQ109 | TMC207 | Projected Inhibition |
|---|---|---|---|---|---|---|---|---|---|
| 0.104 | 0 | 0 | 0 | 0 | 15 | 0 | 0.25 | 0.0085 | 98.2% |
| 0.052 | 0 | 0 | 0 | 0 | 15 | 0 | 0.25 | 0.0085 | 96.8% |
| 0.052 | 0 | 0 | 0 | 0.027 | 15 | 0 | 0.25 | 0 | 93.7% |
| 0.104 | 0 | 0.005 | 0 | 0 | 15 | 0 | 0.25 | 0 | 93.7% |
| 0.104 | 0.24 | 0.005 | 0 | 0 | 0 | 0 | 0 | 0.0085 | 93.0% |
| 0.052 | 0 | 0 | 0 | 0.027 | 0 | 0 | 0.25 | 0.0085 | 92.7% |
| 0.104 | 0 | 0 | 0 | 0 | 7.5 | 0 | 0.25 | 0.0085 | 92.5% |
| 0.104 | 0 | 0.005 | 0 | 0 | 0 | 0 | 0.25 | 0.0085 | 92.5% |
| 0.052 | 0 | 0.005 | 0 | 0 | 15 | 0 | 0.25 | 0 | 92.3% |
| 0.104 | 0 | 0 | 0 | 0.027 | 15 | 0 | 0.25 | 0 | 92.1% |
| 0.052 | 0.24 | 0 | 0 | 0 | 0 | 0 | 0.25 | 0.0085 | 91.7% |
| 0.104 | 0 | 0 | 0 | 0.027 | 0 | 0 | 0.25 | 0.0085 | 91.1% |
| 0.052 | 0 | 0 | 0 | 0 | 7.5 | 0 | 0.25 | 0.0085 | 91.1% |
| 0.052 | 0 | 0.005 | 0 | 0 | 0 | 0 | 0.25 | 0.0085 | 91.1% |
| 0.104 | 0 | 0.0025 | 0 | 0 | 15 | 0 | 0.25 | 0 | 90.8% |
| 0.104 | 0.24 | 0 | 0 | 0 | 0 | 0 | 0.25 | 0.0085 | 90.8% |
| 0.052 | 0 | 0 | 0 | 0.027 | 0 | 0.001 | 0.25 | 0 | 90.8% |
| 0 | 0 | 0 | 0 | 0.027 | 15 | 0 | 0.25 | 0.0085 | 90.7% |
| 0.104 | 0 | 0 | 0 | 0 | 15 | 0 | 0.25 | 0.00425 | 90.6% |
| 0.104 | 0.24 | 0.0025 | 0 | 0 | 0 | 0 | 0 | 0.0085 | 90.1% |
| 0.052 | 0 | 0 | 0 | 0.0135 | 15 | 0 | 0.25 | 0 | 90.1% |
| 0.104 | 0 | 0 | 0 | 0.0135 | 15 | 0 | 0.25 | 0 | 90.0% |
| 0.052 | 0 | 0 | 0 | 0.027 | 7.5 | 0 | 0.25 | 0 | 89.8% |
| 0 | 0 | 0.005 | 0 | 0 | 15 | 0 | 0.25 | 0.0085 | 89.7% |
| 0.104 | 0 | 0.0025 | 0 | 0 | 0 | 0 | 0.25 | 0.0085 | 89.6% |
| 0.052 | 0 | 0.0025 | 0 | 0 | 15 | 0 | 0.25 | 0 | 89.4% |
| 0.104 | 0.24 | 0.005 | 0 | 0.027 | 0 | 0 | 0 | 0 | 89.4% |
| 0.052 | 0 | 0 | 0 | 0 | 15 | 0 | 0.25 | 0.00425 | 89.2% |
| 0.052 | 0 | 0.005 | 0 | 0.027 | 0 | 0 | 0.25 | 0 | 89.2% |
| 0.052 | 0 | 0 | 0 | 0.0135 | 0 | 0 | 0.25 | 0.0085 | 89.0% |
| 0.104 | 0.24 | 0 | 0 | 0 | 0 | 0 | 0.125 | 0.0085 | 89.0% |
| 0.104 | 0 | 0 | 0 | 0.0135 | 0 | 0 | 0.25 | 0.0085 | 88.9% |
| 0.104 | 0.12 | 0 | 0 | 0 | 0 | 0 | 0.25 | 0.0085 | 88.8% |
| 0.052 | 0.12 | 0 | 0 | 0 | 0 | 0 | 0.25 | 0.0085 | 88.5% |
| 0.052 | 0 | 0 | 0 | 0.027 | 0 | 0.0005 | 0.25 | 0 | 88.3% |
| 0.052 | 0.24 | 0.005 | 0 | 0 | 0 | 0 | 0 | 0.0085 | 88.3% |
| 0.052 | 0 | 0.0025 | 0 | 0 | 0 | 0 | 0.25 | 0.0085 | 88.2% |
| 0.104 | 0 | 0 | 0 | 0.027 | 7.5 | 0 | 0.25 | 0 | 88.2% |
| 0.052 | 0.24 | 0 | 0 | 0 | 15 | 0 | 0.25 | 0 | 88.2% |
| 0.052 | 0 | 0 | 0 | 0 | 15 | 0.001 | 0.25 | 0 | 88.1% |
| 0 | 0.24 | 0 | 0 | 0 | 15 | 0 | 0.25 | 0.0085 | 88.0% |
| 0.104 | 0 | 0 | 0 | 0 | 15 | 0 | 0.25 | 0 | 88.0% |
| 0.104 | 0 | 0.005 | 0 | 0 | 7.5 | 0 | 0.25 | 0 | 87.9% |
| 0 | 0 | 0 | 0 | 0.027 | 15 | 0.001 | 0.25 | 0 | 87.7% |
| 0.104 | 0.24 | 0.0025 | 0 | 0.027 | 0 | 0 | 0 | 0 | 87.7% |
| 0.052 | 0.24 | 0.005 | 0 | 0.027 | 0 | 0 | 0 | 0 | 87.7% |
| 0.052 | 0.24 | 0 | 0 | 0.027 | 0 | 0 | 0.25 | 0 | 87.7% |
| 0.104 | 0.12 | 0 | 0 | 0 | 15 | 0 | 0.25 | 0 | 87.6% |
| 0.104 | 0 | 0.005 | 0 | 0.027 | 0 | 0 | 0.25 | 0 | 87.6% |
| 0.052 | 0 | 0.0025 | 0 | 0.027 | 0 | 0 | 0.25 | 0 | 87.5% |
| 0.104 | 0 | 0 | 0 | 0 | 15 | 0.0005 | 0.25 | 0 | 87.5% |

TABLE 3-continued

FSC-projected Inhibition of 3- and 4-drug combinations. Concentration for each drug is expressed in µg/ml.

| CLZ | EMB | PA824 | PAS | PRO | PZA | RIF | SQ109 | TMC207 | Projected Inhibition |
|---|---|---|---|---|---|---|---|---|---|
| 0.104 | 0 | 0 | 0.025 | 0 | 15 | 0 | 0.25 | 0 | 87.4% |
| 0.052 | 0.12 | 0 | 0 | 0 | 15 | 0 | 0.25 | 0 | 87.4% |
| 0 | 0 | 0 | 0 | 0.0135 | 15 | 0 | 0.25 | 0.0085 | 87.3% |
| 0.052 | 0 | 0 | 0 | 0 | 15 | 0.0005 | 0.25 | 0 | 87.3% |
| 0.104 | 0.24 | 0 | 0 | 0 | 15 | 0 | 0.25 | 0 | 87.2% |
| 0.104 | 0 | 0 | 0 | 0 | 15 | 0 | 0.125 | 0.0085 | 87.2% |
| 0.052 | 0.24 | 0 | 0 | 0 | 0 | 0 | 0.125 | 0.0085 | 87.2% |
| 0 | 0 | 0.005 | 0 | 0.027 | 15 | 0 | 0.25 | 0 | 87.1% |
| 0.104 | 0 | 0 | 0 | 0 | 15 | 0.001 | 0.25 | 0 | 87.1% |
| 0 | 0.24 | 0 | 0 | 0.027 | 0 | 0 | 0.25 | 0.0085 | 87.0% |
| 0 | 0.24 | 0.005 | 0 | 0 | 0 | 0 | 0.25 | 0.0085 | 87.0% |
| 0.104 | 0 | 0 | 0.05 | 0 | 15 | 0 | 0.25 | 0 | 86.9% |
| 0 | 0 | 0.0025 | 0 | 0 | 15 | 0 | 0.25 | 0.0085 | 86.9% |
| 0.052 | 0 | 0 | 0 | 0.027 | 0 | 0 | 0.25 | 0.00425 | 86.8% |
| 0.104 | 0 | 0 | 0 | 0.027 | 0 | 0.001 | 0.25 | 0 | 86.8% |
| 0 | 0 | 0 | 0 | 0.027 | 7.5 | 0 | 0.25 | 0.0085 | 86.8% |
| 0.052 | 0.12 | 0 | 0 | 0.027 | 0 | 0 | 0.25 | 0 | 86.8% |
| 0.052 | 0 | 0 | 0 | 0 | 0 | 0.001 | 0.25 | 0.0085 | 86.8% |
| 0.104 | 0 | 0 | 0 | 0 | 0 | 0 | 0.25 | 0.0085 | 86.7% |
| 0 | 0 | 0.005 | 0 | 0.027 | 0 | 0.001 | 0.25 | 0 | 86.6% |
| 0.052 | 0 | 0 | 0 | 0 | 15 | 0 | 0.25 | 0 | 86.6% |
| 0.052 | 0 | 0.005 | 0 | 0 | 7.5 | 0 | 0.25 | 0 | 86.5% |
| 0.104 | 0.24 | 0.005 | 0 | 0 | 15 | 0 | 0 | 0 | 86.5% |
| 0.052 | 0.24 | 0 | 0 | 0 | 0 | 0.001 | 0.25 | 0 | 86.4% |
| 0.104 | 0 | 0 | 0 | 0 | 0 | 0.0005 | 0.25 | 0.0085 | 86.3% |
| 0.104 | 0 | 0 | 0.025 | 0 | 0 | 0 | 0.25 | 0.0085 | 86.2% |
| 0 | 0 | 0.005 | 0 | 0.027 | 0 | 0 | 0.25 | 0.0085 | 86.2% |
| 0.052 | 0 | 0 | 0 | 0 | 0 | 0.0005 | 0.25 | 0.0085 | 86.1% |
| 0.052 | 0.24 | 0.0025 | 0 | 0.027 | 0 | 0 | 0 | 0 | 86.0% |
| 0.052 | 0 | 0 | 0.025 | 0 | 15 | 0 | 0.25 | 0 | 86.0% |
| 0.052 | 0.24 | 0 | 0 | 0.027 | 0 | 0 | 0.125 | 0 | 86.0% |
| 0 | 0.12 | 0 | 0 | 0 | 15 | 0 | 0.25 | 0.0085 | 86.0% |
| 0.052 | 0 | 0 | 0 | 0.027 | 0 | 0 | 0.25 | 0 | 85.9% |
| 0 | 0 | 0 | 0 | 0.027 | 15 | 0.0005 | 0.25 | 0 | 85.8% |
| 0.104 | 0 | 0 | 0 | 0 | 0 | 0.001 | 0.25 | 0.0085 | 85.8% |
| 0.104 | 0 | 0 | 0.05 | 0 | 0 | 0 | 0.25 | 0.0085 | 85.7% |
| 0.104 | 0.24 | 0.005 | 0 | 0 | 0 | 0.001 | 0 | 0 | 85.6% |
| 0.104 | 0 | 0 | 0 | 0.027 | 0 | 0.0005 | 0.25 | 0 | 85.5% |
| 0 | 0 | 0 | 0 | 0.027 | 7.5 | 0.001 | 0.25 | 0 | 85.5% |
| 0.052 | 0 | 0 | 0.05 | 0 | 15 | 0 | 0.25 | 0 | 85.5% |
| 0 | 0 | 0.0025 | 0 | 0.027 | 15 | 0 | 0.25 | 0 | 85.5% |
| 0.052 | 0.24 | 0.0025 | 0 | 0 | 0 | 0 | 0 | 0.0085 | 85.4% |
| 0.052 | 0 | 0 | 0 | 0.0135 | 0 | 0.001 | 0.25 | 0 | 85.4% |
| 0.052 | 0 | 0 | 0.025 | 0.027 | 0 | 0 | 0.25 | 0 | 85.4% |
| 0.052 | 0 | 0 | 0 | 0 | 0 | 0 | 0.25 | 0.0085 | 85.3% |
| 0.052 | 0 | 0 | 0 | 0.0135 | 7.5 | 0 | 0.25 | 0 | 85.3% |
| 0.104 | 0 | 0 | 0 | 0.027 | 0 | 0 | 0.25 | 0.00425 | 85.3% |
| 0.104 | 0 | 0 | 0 | 0.0135 | 7.5 | 0 | 0.25 | 0 | 85.2% |
| 0 | 0.24 | 0.005 | 0 | 0.027 | 0 | 0.001 | 0 | 0 | 85.2% |
| 0 | 0.24 | 0 | 0 | 0 | 0 | 0.001 | 0.25 | 0.0085 | 85.1% |
| 0.104 | 0 | 0.0025 | 0 | 0 | 7.5 | 0 | 0.25 | 0 | 85.1% |
| 0 | 0 | 0.0025 | 0 | 0.027 | 0 | 0.001 | 0.25 | 0 | 85.0% |
| 0.052 | 0 | 0.005 | 0 | 0.0135 | 0 | 0 | 0.25 | 0 | 85.0% |
| 0 | 0.12 | 0 | 0 | 0.027 | 0 | 0 | 0.25 | 0.0085 | 85.0% |

CUTOFF STANDARD REGIMEN: EMB (0.24) INH (0.007) PZA (15) RIF (0.001) = 85.0%

Efficacy of FSC Regimen I (Combination #47) in a Mouse Model of Pulmonary TB (Mouse In Vivo Experiment 1)

Sixty-five eight-week old, female, pathogen-free Balb/c mice were purchased from Taconic. The mice were housed in groups of 5 with unlimited access to food and water. After a 7-day quarantine period, mice were infected with an aerosol generated from about 20 ml suspension of about $1.875 \times 10^6$ *Mycobacterium tuberculosis*, Erdman strain. One day later, two mice were euthanized to determine the initial number of bacteria in their lungs. The two mice had 2.22±0.09 log (Mean±Standard Error (SE)) colony-forming units (CFU) of *M. tuberculosis*/lung (total lung). After two weeks, three mice were euthanized to determine the number of bacteria in the lungs at that time point, and the three mice had 6.24±0.05 log CFU (Mean±SE)/total lung. The mice were then divided into 12 treatment groups as follows:

Group A: Sham treated with vehicle only (5 mice)

Group B: RIF/EMB/INH/PZA (Standard Regimen) by gavage 5×/week for 4 weeks (5 mice)

Group C: CLZ/EMB/PRO/PZA (High/Low/Low/High) by gavage 5×/wk for 4 wks (5 mice)

Group D: CLZ/EMB/PRO/PZA (High/Low/High/Low) by gavage 5×/wk for 4 wks (5 mice))

Group E: CLZ/EMB/PRO/PZA (High/High/Low/Low) by gavage 5×/wk for 4 wks (5 mice)

Group F: CLZ/EMB/PRO/PZA (High/High/High/High) by gavage 5×/wk for 4 wks (5 mice)
Group G: CLZ/EMB/PRO/PZA (High/High/High/Low) by gavage 5×/wk for 4 wks (5 mice)
Group H: CLZ/EMB/PRO/PZA (High/High/Low/High) by gavage 5×/wk for 4 wks (5 mice)
Group I: CLZ/EMB/PRO/PZA (High/Low/High/High) by gavage 5×/wk for 4 wks (5 mice)
Group J: CLZ/EMB/PRO/PZA (High/High/Middle/Middle) by gavage 5×/wk for 4 wks (5 mice)
Group K: CLZ/EMB/PRO/PZA (High/Middle/High/Middle) by gavage 5×/wk for 4 wks (5 mice)
Group L: CLZ/EMB/PRO/PZA (High/Middle/Middle/High) by gavage 5×/wk for 4 wks (5 mice)

The mice were treated by oral gavage five times per week (Monday-Friday) for 4 weeks with the drugs at High, Middle and Low doses, as indicated above. The amount of drug corresponding to the high, middle and low doses is as follows:

TABLE 4

Drugs and drug doses for FSC Regimen I

| Drug | Abbr. | Source | Stock | High | Middle | Low |
|---|---|---|---|---|---|---|
| | | | | \multicolumn{3}{c}{mg/kg} | 
| Clofazimine | CLZ | Sigma C8895-1G Lot SLBB7964V | 150 mg/30 ml of 0.05% Agarose, (No DMSO) | 25 | | |
| Ethambutol | EMB | Sigma, E4630, Lot 126H0774 | 60 mg/ml in 0.15% agarose with 20% DMSO [3×-high] | 100 | 33.3 | 11.1 |
| Prothionamide | PRO | Santa Cruz sc204865A, Lot E3112 | 45 mg/ml in 0.15% agarose with 20% DMSO [3×-high] | 75 | 25 | 8.3 |
| Pyrazinamide | PZA | Sigma, P7136, Lot 44H0049 | 270 mg/ml in 0.15% agarose with 20% DMSO [3×-high] | 450 | 150 | 50 |

The group receiving the Standard Regimen received the drugs at the following doses:

TABLE 5

Drugs and drug doses for Standard Regimen
Control Standard Regimen

| Drug | Abbr. | Source | Stock | mg/kg |
|---|---|---|---|---|
| Ethambutol | EMB | See above | 60 mg/ml in 0.15% agarose with 20% DMSO [3×] | 100 |
| Isoniazid | INH | Sigma-I3377-50G Lot 075K1581 | 15 mg/ml in 0.15% agarose with 20% DMSO [3×] | 25 |
| Pyrazinamide | PZA | See above | 270 mg/ml in 0.15% agarose with 20% DMSO [9×] | 150 |
| Rifampicin | RIF | Sigma (4° C. dessicator) | 6 mg/3 ml of water with 10% DMSO | 10 |

Mice were gavaged twice at each sitting as follows: Group B was administered EMB/INH/PZA first followed by about 45 minutes or more later with RIF. Groups C-L were administered EMB/PRO/PZA first followed by about 45 minutes or more later with CLZ. Group A was administered vehicle I (agarose solution) first followed by about 45 minutes or more later with vehicle II (water).

Three days after the last treatment dose, all mice were euthanized, their lung, liver, and spleen removed aseptically, and the lungs inspected for pathology. The organs were homogenized in phosphate-buffered saline (PBS), and the homogenates serially diluted and plated on 7H11—0.4% charcoal agar containing Ampicillin (about 12.5 µg/ml), Amphotericin B (about 5 µg/ml), and Polymyxin B (about 20 Units/ml). The plates were incubated at about 37° C. in about 5% $CO_2$-95% air atmosphere for 4 weeks, after which the number of CFU of *M. tuberculosis* on each plate was counted.

On inspection, mice in Group A (Sham treated) had the most pathology as evidenced by large numbers of tubercles on the lung. Mice in Group B (Standard Regimen) had somewhat less pathology than mice in Group A. Mice in Groups C-L had less pathology than Group B as evidenced by markedly fewer tubercles.

With respect to the organ burden of *M. tuberculosis* in the lung, the mice had the following CFU counts in their lungs:

TABLE 6

*M. tuberculosis* CFU per lung from mice after 4 weeks of treatment

| Group | Mean Log CFU in lung | Standard Error (Log) |
|---|---|---|
| A | 6.67 | 0.09 |
| B | 4.24 | 0.08 |
| C | 2.88 | 0.11 |
| D | 3.83 | 0.16 |
| E | 3.64 | 0.10 |
| F | 2.45 | 0.11 |
| G | 3.97 | 0.09 |
| H | 2.77 | 0.07 |
| I | 2.69 | 0.07 |
| J | 3.60 | 0.10 |
| K | 3.78 | 0.06 |
| L | 2.80 | 0.05 |

With respect to the organ burden of *M. tuberculosis* in the liver and spleen, just the sham-treated mice had appreciable numbers. Those mice had 4.07±0.19 (Mean±SE) log CFU in the liver and 5.03=0.11 (Mean±SE) log in the spleen. All treated groups had less than about 1.7 log CFU in the spleen and less than about 2.2 log CFU in the liver.

Figure 7:
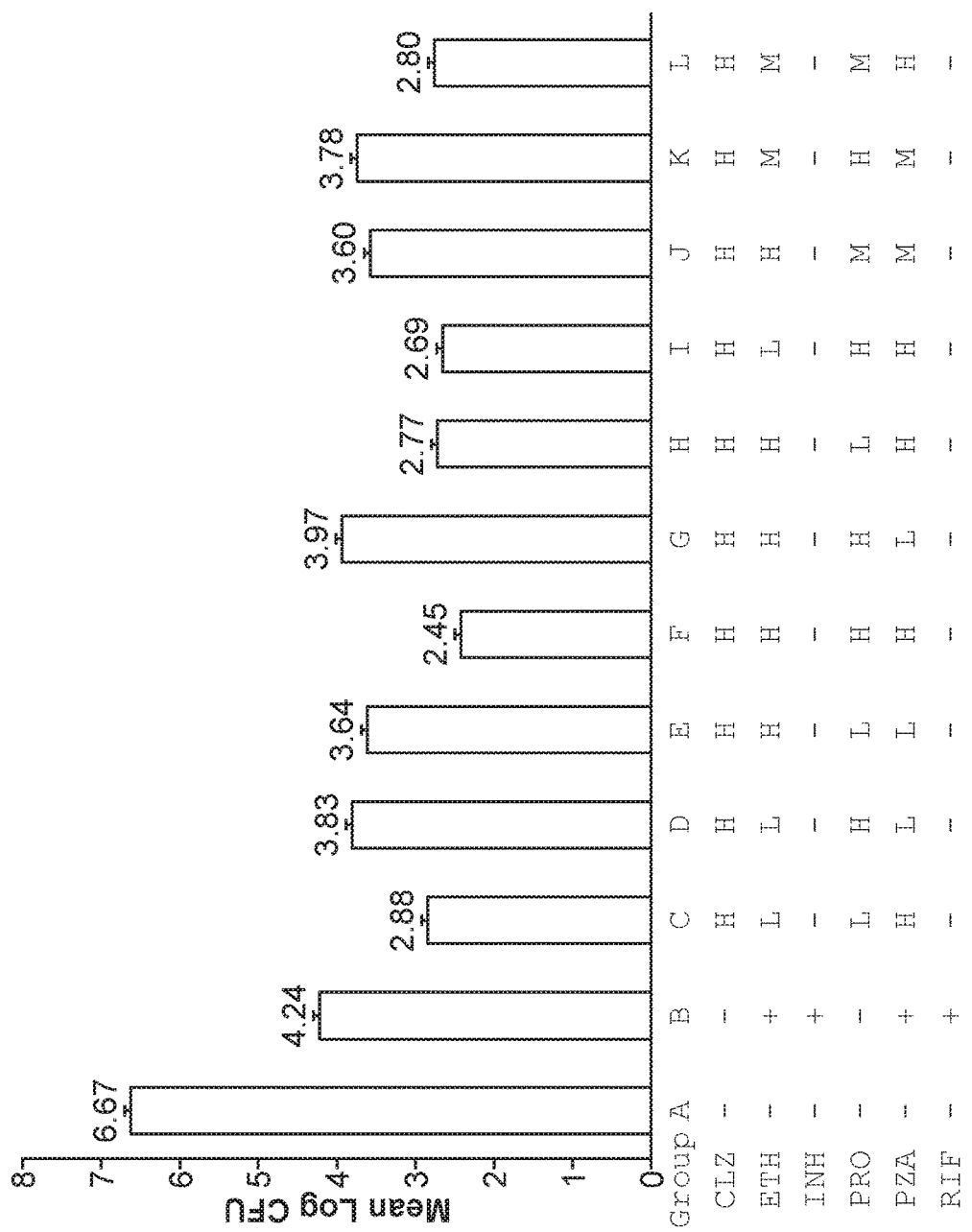
FIG. 7 shows *M. tuberculosis* CFU per lung from mice after 4 weeks of treatment.
Figure 8:
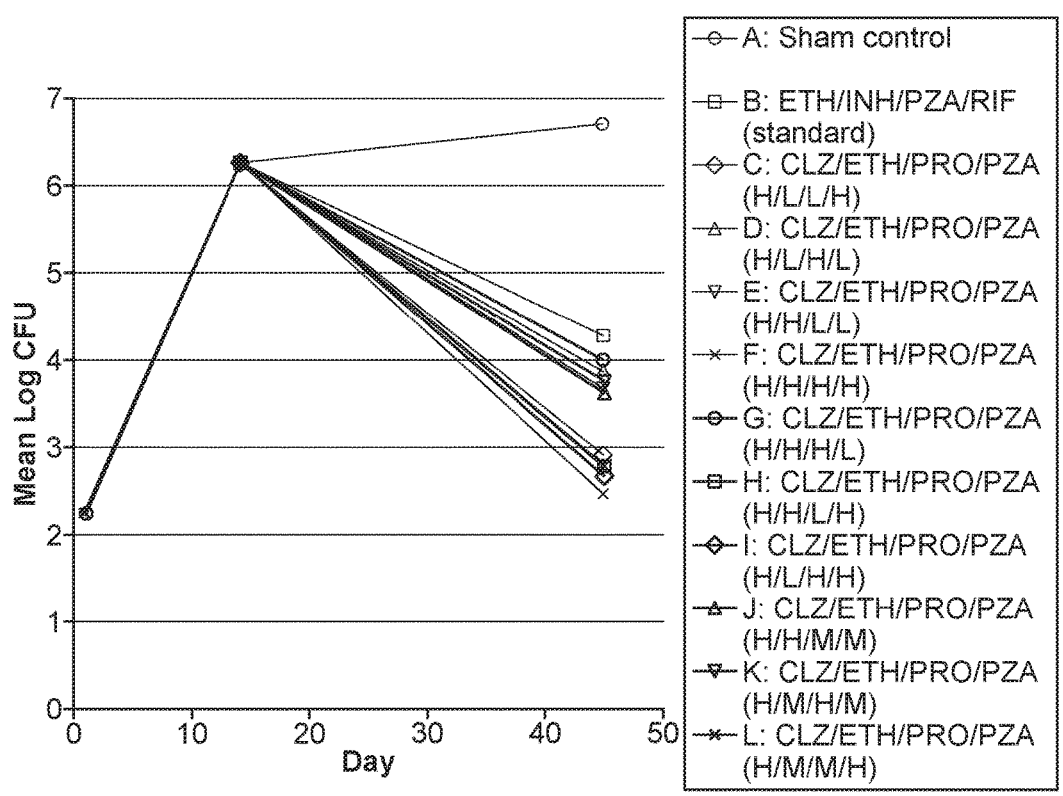
FIG. 8 shows tuberculosis CFU per lung from mice that are sham-treated, treated with Standard Regimen or treated with FSC Regimen I with the drug at high (H), middle (M) or low (L) dose five times per week for 4 weeks.

The lung data at the time of euthanasia is presented graphically in FIG. 7. FIG. 8 shows the data at the start of the experiment (Day 0), 14 days after challenge (Day 14) and 28 days after the start of treatment (Day 42). In FIG. 8, *M. tuberculosis* CFU per lung from mice in groups A-L over the course of infection and treatment with the drugs at high (H), middle (M) or low (L) doses. Mice were infected with

*M. tuberculosis* Erdman by aerosol (Day 0), treated starting 14 days after challenge for 4 weeks (Days 14-39) and euthanized 3 days after the end of treatment (Day 42) to determine bacterial burden in the lung. Mice in groups were treated with FSC Regimen I, a drug combination of CLZ, EMB, PRO, and PZA with the individual drugs at high (H), middle (M) or low dose, as indicated.

Summary and Conclusions.

Mice in all 10 FSC Regimen I-treated groups had fewer CFU in their lungs than mice treated with the Standard. Regimen. Mice in the best FSC Regimen I group had about 1.8 logs fewer CFU in their lungs than mice treated with the Standard Regimen. Mice in the FSC Regimen I-treated groups had less lung pathology than mice in the sham group and mice in the group treated with the Standard Regimen. Thus FSC Regimen I was markedly superior to the Standard Regimen.

Efficacy of FSC Regimen II (Combination #48) in a Mouse Model of Pulmonary TB (Mouse In Vivo Experiment 2)

Sixty-five eight-week old, female, pathogen-free Balb/c mice were purchased from Taconic. The mice were housed in groups of 5 with unlimited access to food and water. After a 7-day quarantine period, mice were infected with an aerosol generated from about 20 rat suspension of about $1.875 \times 10^6$ *Mycobacterium tuberculosis*, Erdman strain. One day later, two mice were euthanized to determine the initial number of bacteria in their lungs. The two mice had $2.36 \pm 0.11$ log (Mean±SE) CFU of *M. tuberculosis*/lung (total lung). After two weeks, three mice were euthanized to determine the number of bacteria in the lungs at that time point, and the three mice had $6.09 \pm 0.04$ log CFU (Mean±SE)/total lung. The mice were then divided into 12 treatment groups as follows:

Group A: Sham treated with vehicle only (5 mice)

Group B: RIF/EMB/INH/PZA (Standard Regimen) by gavage 5×/week for 4 wks (5 mice)

Group C: CLZ/EMB/TMC/PZA (High/Low/Low/High) by gavage 5×/wk for 4 wks (5 mice)

Group D: CLZ/EMB/TMC/PZA (High/Low/High/Low) by gavage 5×/wk for 4 wks (5 mice))

Group E: CLZ/EMB/TMC/PZA (High/High/Low/Low) by gavage 5×/wk for 4 wks (5 mice)

Group F: CLZ/EMB/TMC/PZA (High/High/High/High) by gavage 5×/wk for 4 wks (5 mice)

Group G: CLZ/EMB/TMC/PZA (High/High/High/Low) by gavage 5×/wk for 4 wks (5 mice)

Group H: CLZ/EMB/TMC/PZA (High/High/Low/High) by gavage 5×/wk for 4 wks (5 mice)

Group I: CLZ/EMB/TMC/PZA (High/Low/High/High) by gavage 5×/wk for 4 wks (5 mice)

Group J: CLZ/EMB/TMC/PZA (High/High/Middle/Middle) by gavage 5×/wk for 4 wks (5 mice)

Group K: CLZ/EMB/TMC/PZA (High/Middle/High/Middle) by gavage 5×/wk for 4 wks (5 mice)

Group L: CLZ/EMB/TMC/PZA (High/Middle/Middle/High) by gavage 5×/wk for 4 wks (5 mice)

The mice were treated by oral gavage five times per week (Monday-Friday) for 4 weeks with the drugs at High, Middle and Low doses, as indicated above. The amount of drug corresponding to the high, middle and low doses is as follows:

TABLE 7

Drugs and drug doses for FSC Regimen II

| | | | | Experimental TB Drug Regimens | mg/kg | | |
|---|---|---|---|---|---|---|---|
| Drug | Abbr. | Source | Stock | | High | Middle | Low |
| Clofazimine | CLZ | Sigma C8895-1G Lot SLBB7964V | 150 mg/30 ml of 0.15% Agarose (No DMSO) | | 25 | | |
| Ethambutol | EMB | Sigma, E4630, Lot 126H0774 | 60 mg/ml in 0.15% agarose with 20% DMSO [3×-high] | | 100 | 33.1 | 11.1 |
| TMC-207 | TMC | TB Alliance | 45 mg/ml in 0.15% agarose with 20% DMSO [3×-high] | | 50 | 16.7 | 5.6 |
| Pyrazinamide | PLA | Sigma, P7136, Lot 449H0049 | 270 mg/ml in 0.15% agarose with 20% DMSO [3×-high] | | 450 | 150 | 50 |

The group receiving the Standard Regimen received the drugs at the same doses shown in Table 5.

Mice were gavaged twice at each sitting as follows: Group B was administered EMB/INH/PZA first followed by about 45 minutes or more later with RIF. Groups C-L were administered. EMB/TMC/PZA first followed by about 45 minutes or more later with CLZ. Group A was administered as described above.

Three days after the last treatment dose, all mice were euthanized, their lung, liver, and spleen removed aseptically, and the lungs inspected for pathology. The organs were homogenized in PBS, and the homogenates serially diluted and plated on 7H11—0.4% charcoal agar containing Ampicillin (about 12.5 µg/ml), Amphotericin B (about 5 µg/ml), and Polymyxin B (about 20 Units/ml). The plates were incubated at about 37° C. in about 5% $CO_2$-95% air atmosphere for 4 weeks, after which the number of CFU of *M. tuberculosis* on each plate was counted.

On inspection, mice in Group A (Sham treated) had the most pathology as evidenced by large numbers of tubercles on the lung. Mice in Group B (Standard Regimen) had somewhat less pathology than mice in Group A. Mice in Groups C-L had less pathology than Group B as evidenced by markedly fewer tubercles.

With respect to the organ burden of *M. tuberculosis* in the lung, the mice had the following CRT counts in their lungs:

TABLE 8

*M. tuberculosis* CFU per lung from mice that are sham-treated, treated with Standard Regimen or FSC Regimen 11 for 4 weeks

| Group | Mean Log CFU in lung | Standard Error (Log) |
|---|---|---|
| A | 6.71 | 0.05 |
| B | 3.94 | 0.03 |
| C | 1.02 | 0.12 |
| D | 0.82 | 0.06 |
| E | 1.96 | 0.09 |
| F | 0.76 | 0.01 |
| G | 0.77 | 0.00 |
| H | 1.16 | 0.15 |
| I | 0.77 | 0.01 |
| J | 0.77 | 0.01 |
| K | 0.76 | 0.01 |
| L | 0.78 | 0.01 |

With respect to the organ burden of *M. tuberculosis* in the liver and spleen, just the sham-treated mice had appreciable numbers. Those mice had 4.26±0.30 (Mean±SE) log CFU in the liver and 4.85±0.13 (Mean±SE) log in the spleen. All treated groups had less than about 1.04 log CFU in the spleen and less than about 0.89 log CFU in the liver. *M. tuberculosis* CFU per lung from mice that are sham-treated, treated with Standard Regimen or treated with FSC Regimen II with the drug at high (H), middle (M) or low (L) dose five times per week for 4 weeks.

Figure 9:
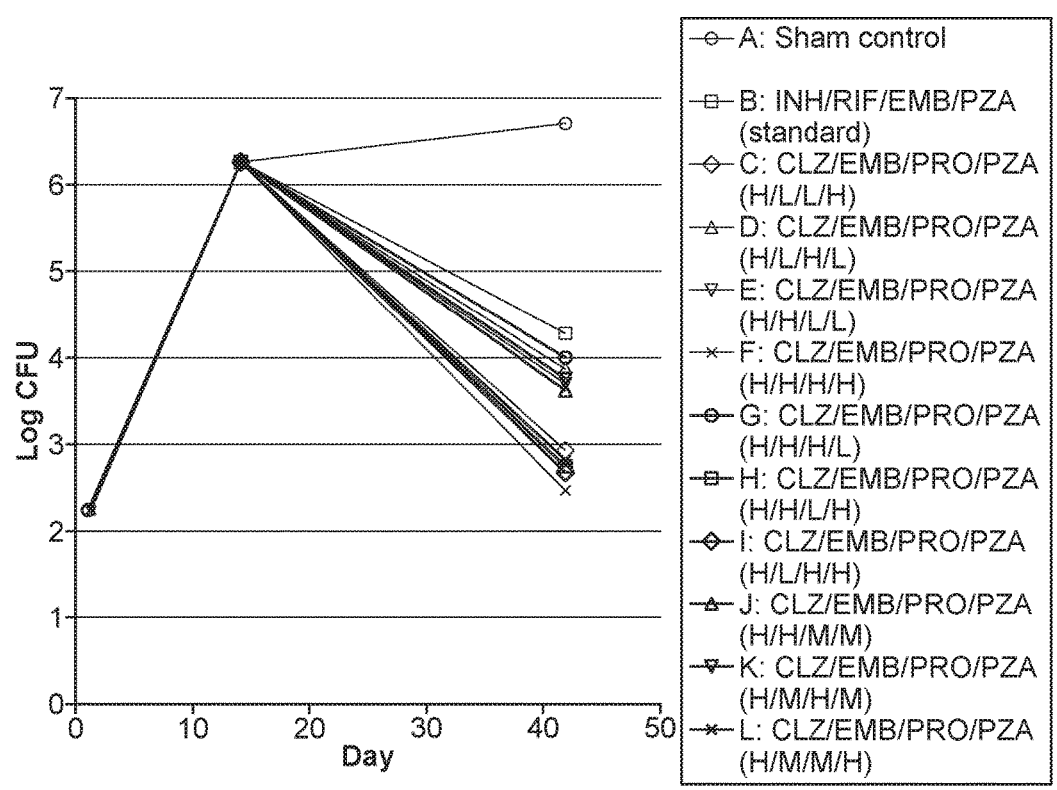
FIG. 9 shows *M. tuberculosis* CFU per lung from mice in groups A-L over the course of infection and treatment with the drugs at high (H), middle (M) or low (L) doses. Mice were infected with *M. tuberculosis* Erdman by aerosol (Day 0), treated starting 14 days after challenge for 4 weeks (Days 14-39) and euthanized 3 days after the end of treatment (Day 42) to determine bacterial burden in the lung. Mice in groups C-L were treated with FSC Regimen I, a drug combination of CLZ, EMB, PRO, and PZA with the individual drugs at high (H), middle (M) or low (L) dose, as indicated.
Figure 10:
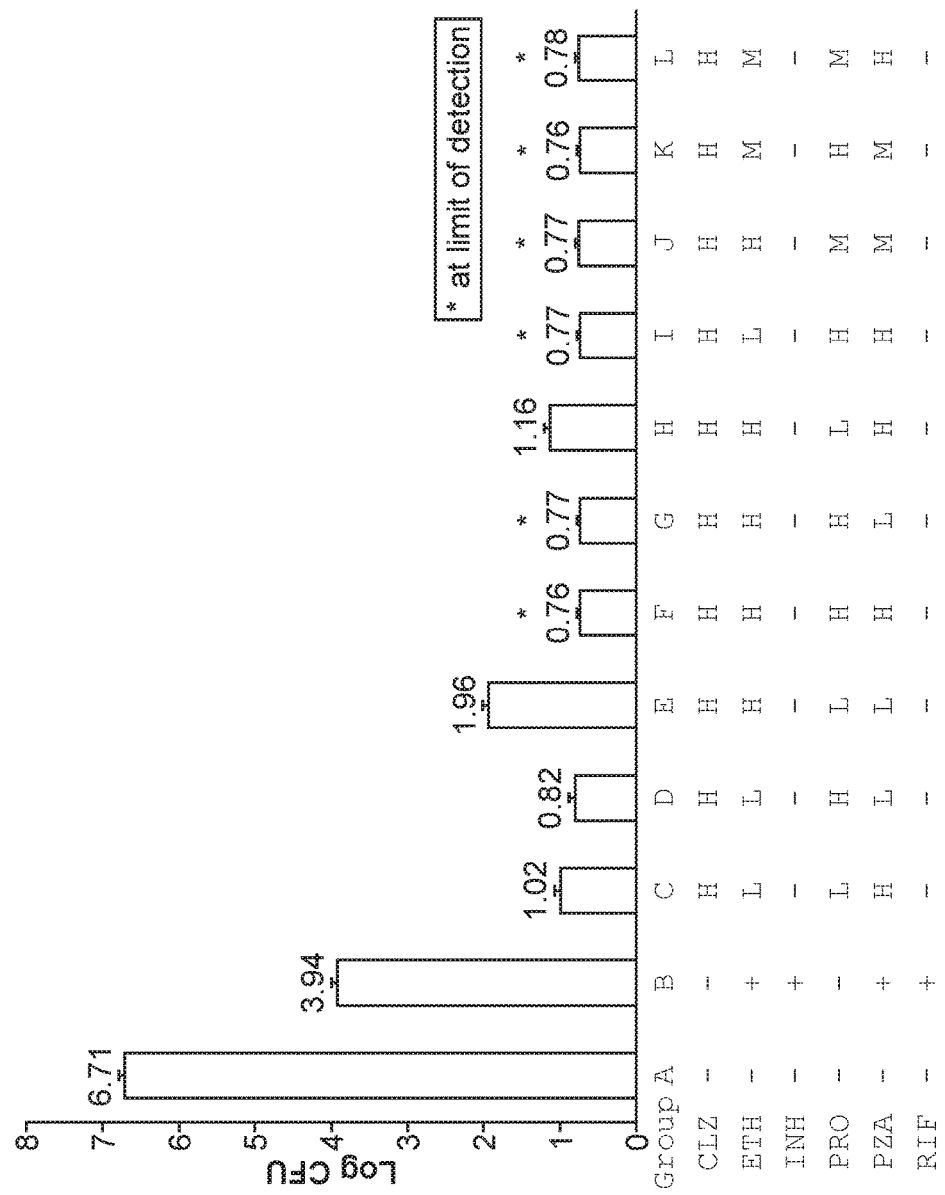
FIG. 10 shows *M. tuberculosis* CFU per lung from mice that are sham-treated, treated with Standard Regimen or treated with FSC Regimen II with the drug at high (H), middle (M) or low (L) dose five times per week for 4 weeks.

The lung data at the time of euthanasia is presented graphically in FIG. 8. In FIG. 8, *M. tuberculosis* CFU per lung from mice that are sham-treated, treated with Standard Regimen or treated with FSC Regimen II with the drug at high (H), middle (M) or low (L) dose five times per week for 4 weeks. FIG. 9 shows the data at the start of the experiment (Day 0), 14 days after challenge (Day 14) and 28 days after the start of treatment (Day 42). In FIG. 9, *M. tuberculosis* CFU per lung from mice in groups A-L over the course of infection and treatment. Mice were infected with *M. tuberculosis* Erdman by aerosol (Day 0), treated starting 14 days after challenge for 4 weeks (Days 14-39) and euthanized 3 days after the end of treatment (Day 42) to determine bacterial burden in the lung. Mice in groups C-L were treated with FSC Regimen II, a drug combination consisting CLZ, EMB, TMC, and PZA with the individual drugs at high (H), middle (M) or low (L) dose.

Summary and Conclusions.

Mice infected with *M. tuberculosis* and treated with all 10 FSC Regimen II-treated groups had fewer CFU in their lungs than mice treated with the Standard. Regimen. Mice in the best FSC Regimen II group had about 3.2 logs fewer CFU in their lungs than mice treated with the Standard Regimen. Mice in the FSC Regimen II-treated groups had less lung pathology than mice in the sham group and mice in the group treated with the Standard Regimen. Thus FSC Regimen II was markedly superior to the Standard Regimen.

Efficacy and Relapse of FSC Regimens I, IIA, and IIB in a Mouse Model of Pulmonary TB (Mouse In Vivo Experiment 3)

One hundred and thirty seven eight-week old, female, pathogen-free Balb/c mice were purchased from Harlan. The mice were housed with unlimited access to food and water. After a 7-day quarantine period, mice were infected with *Mycobacterium tuberculosis*, Erdman strain. One day later, two mice were euthanized to determine the initial number of bacteria in their lungs. The two mice had 2.07±0.08 log (Mean±SE) CFU of *M. tuberculosis*/lung (total lung). After two weeks, three mice were euthanized to determine the number of bacteria in the lungs at that time point, and the three mice had 6.04±0.08 log CFU (Mean±SE)/total lung. The mice were then divided into 10 treatment groups as follows:

Efficacy Study

Group A: Sham treated with vehicle only by gavage 5×/wk for 2, 3, 4, 6 or 8 wks (25 mice)

Group B: RIF/EMB/INH/PZA (Standard Regimen) by gavage 5×/wk for 2, 3, 4, 6 or 8 wks (25 mice)

Group C: RIF/EMB/INH/PZA (Enhanced Standard Regimen) by gavage 5×/wk for 3, 4 or 8 wks (15 mice)

Group D: CLZ/EMB/PRO/PZA (FSC Regimen I) by gavage 5×/wk for 4, 6 or 8 wks (15 mice)

Group E: CLZ/EMB/TMC/PZA (FSC Regimen IIA) by gavage 5×/wk for 2, 3, 4, 6 wks (20 mice)

Group F: CLZ/EMB/TMC/PZA (FSC Regimen IIB) by gavage 5×/wk for 2 or 3 wks (10 mice)

Relapse Study

Group H: CLZ/EMB/TMC/PZA (FSC Regimen IIA) by gavage 5×/wk for 3 wks (8 mice)

Group I: CLZ/EMB/TMC/PZA (FSC Regimen IIA) by gavage 5×/wk for 4 wks (7 mice)

Group J: CLZ/EMB/TMC/PZA (FSC Regimen IIA) by gavage 5×/wk for 6 wks (5 mice)

The mice were treated by oral gavage five times per week (Monday-Friday) for 2-8 weeks with Standard Regimen, Enhanced Standard Regimen, FSC Regimen I, FSC Regimen IIA, or FSC Regimen IIB as indicated above. The amount of drug in each treatment regimen is as follows:

TABLE 9

List of Standard Regimen controls and Experimental FSC Regimens

| Experimental TB Drug Regimens | Drug Concentration (mg/kg) | | | | |
|---|---|---|---|---|---|
| | CLZ | EMB | PRO | TMC | PZA |
| FSC Regimen I | 25 | 100 | 75 | | 450 |
| FSC Regimen IIA | 25 | 100 | | 16.7 | 150 |
| FSC Regimen IIB | 25 | 100 | | 16.7 | 450 |

| Control Standard Regimens | Drug Concentration (mg/kg) | | | |
|---|---|---|---|---|
| | RIF | EMB | INH | PZA |
| Standard Regimen | 10 | 100 | 25 | 150 |
| Enhanced Standard Regimen | 10 | 100 | 25 | 450 |

Drugs and drug doses in each combinational drug regimen are shown in FIG. 12.

For the efficacy part of the study, mice in Groups A-F were euthanized three days after the last treatment dose, their lungs were removed aseptically and inspected for pathology, homogenized in PBS, and serially diluted and plated on 7H11—0.4% charcoal agar containing Ampicillin (about 12.5 μg/ml), Amphotericin B (about 5 μg/ml), and Polymyxin B (about 20 Units/ml). The plates were incubated at about 37° C. in about 5% $CO_2$-95% air atmosphere for 4 weeks, after which the number of CFU of *M. tuberculosis* on each plate was counted.

For the relapse part of the study, mice in Groups H-J, all treated with FSC Regimen IIA for various lengths of time, were euthanized 3 months after the end of treatment, their lungs and spleens homogenized and CFU per lung and spleen determined by plating the entire organ.

FIG. 13 shows the scheme of Mouse in vivo testing for this example. On inspection, mice in Group A (Sham treated) had the most pathology as evidenced by large numbers of tubercles on the lung. Mice in Group B (Standard Regimen) had somewhat less pathology than mice in Group A. Mice in Group C (Enhanced Standard Regimen) had less pathology than Group B as evidenced by markedly fewer tubercles. Mice in Groups D-F (FSC Regimens) had the fewest lung lesions.

With respect to the organ burden of M. tuberculosis in the lung, mice treated with FSC Regimens I, IIA, and IIB had fewer CFU in their lungs than mice treated with the Standard Regimen or the Enhanced Standard Regimen (high PZA).

FSC Regimen II had a greater efficacy than FSC Regimen I. FSC Regimen IIB lowered CFU faster than FSC Regimen IIA.

Figure 14:
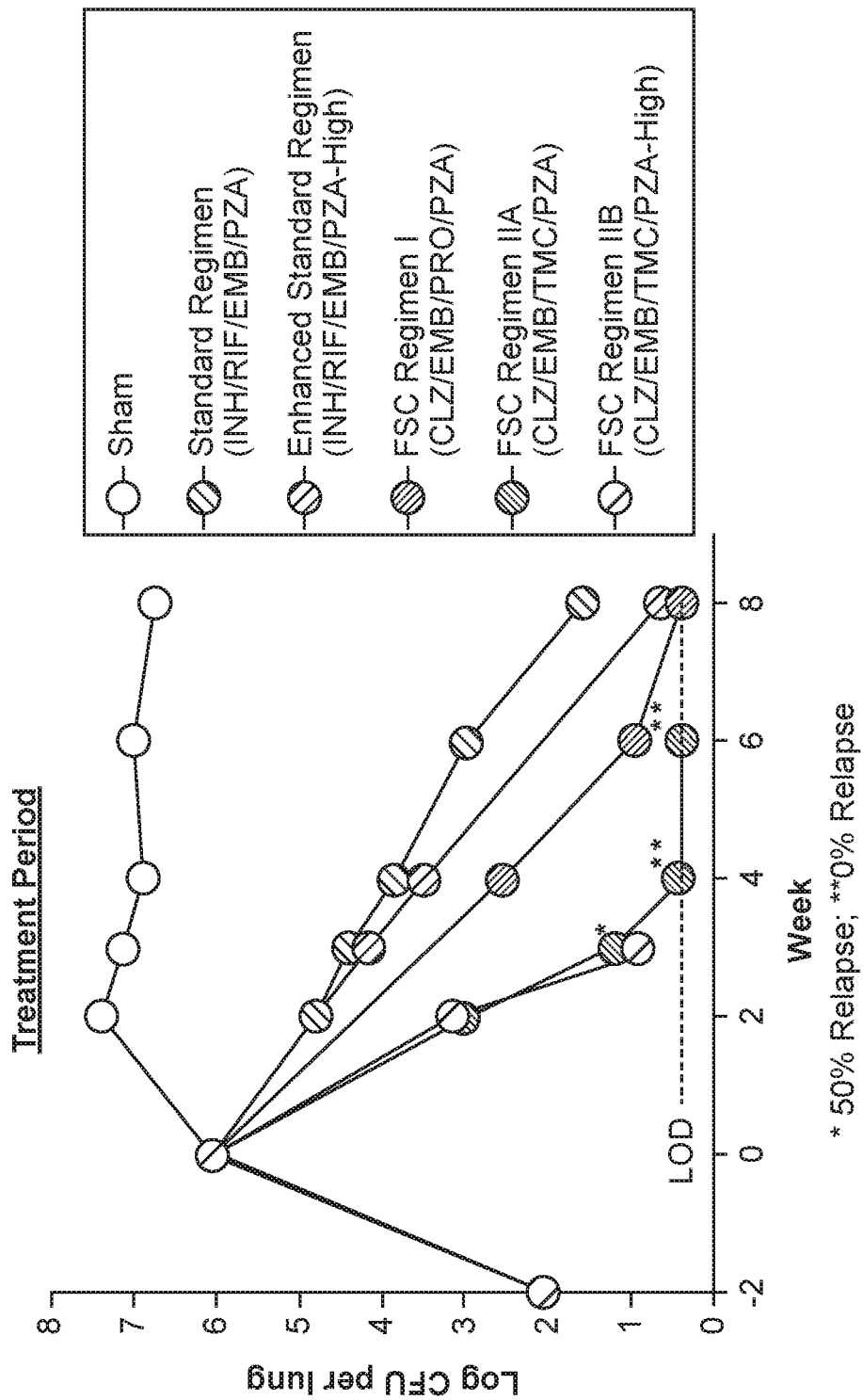
FIG. 14 shows the efficacy of FSC Regimens I and IIA/B over 8 weeks of treatment. *M. tuberculosis* CFU per lung from mice in groups A-F over the course of infection and treatment. Mice were infected with *M. tuberculosis* Erdman by aerosol (Day 0), treated starting 14 days after challenge for up to 8 weeks (Days 14-67) and euthanized 3 days after the end of treatment (Day 70) to determine bacterial burden in the lung. Mice were treated with FSC Regimen I, IIA, or IIB as indicated. LOD: limit of detection.

FIG. 14 shows the efficacy of FSC Regimens I and IIA/B over 8 weeks of treatment. In FIG. 14, M. tuberculosis CFU per lung from mice in groups A-F over the course of infection and treatment. Mice were infected with M. tuberculosis Erdman by aerosol (Day 0), treated starting 14 days after challenge for up to 8 weeks (Days 14-67) and euthanized 3 days after the end of treatment (Day 70) to deter bacterial burden in the lung. Mice were treated with FSC Regimen I, IIA, or IIB as indicated, LOD: limit of detection.

Figure 15:
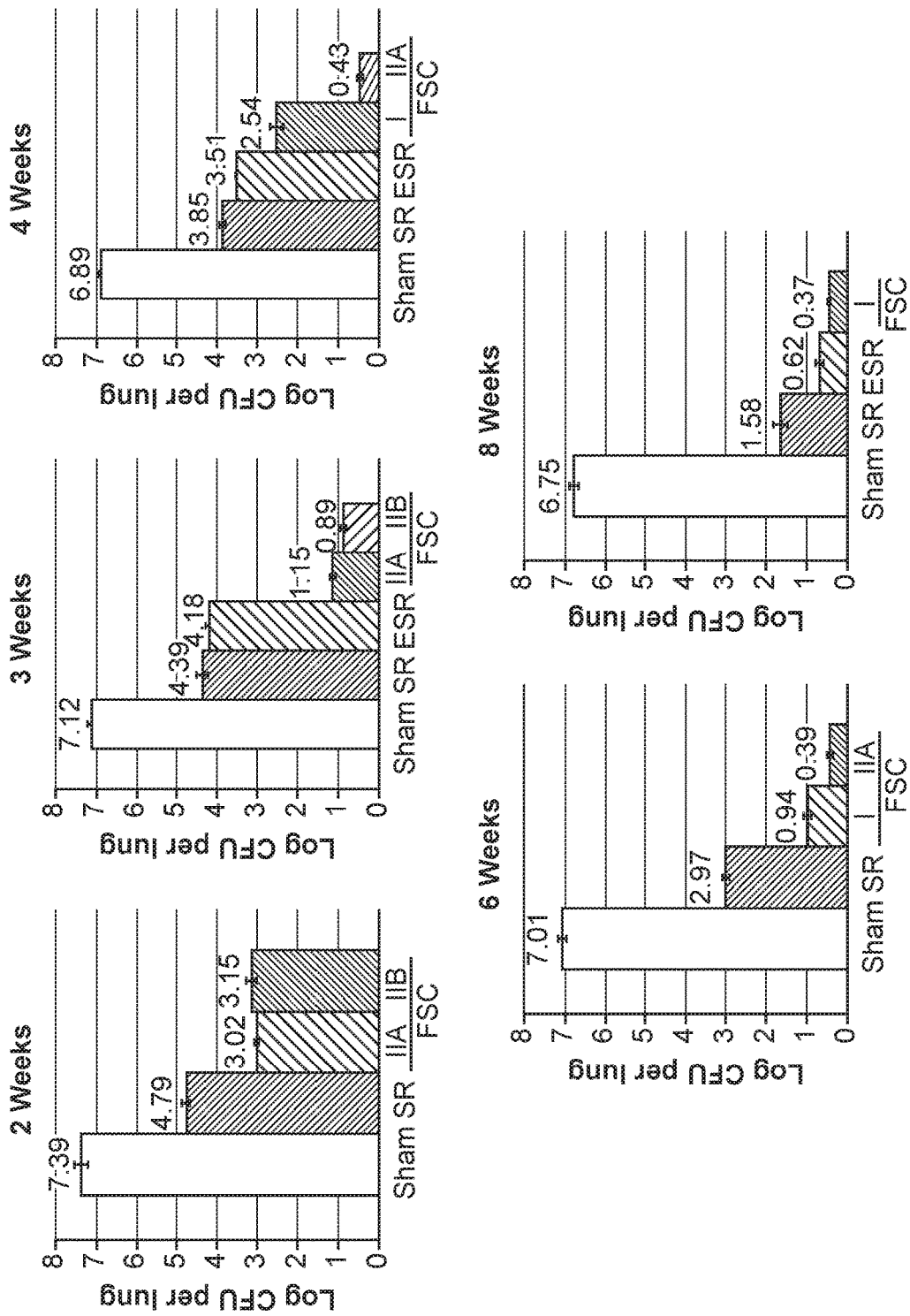
FIG. 15 shows the efficacy of FSC Regimens I and IIA/B after 2, 3, 4, 6 or 8 weeks of treatment. CFU in the lungs of mice that were sham-treated (Sham), treated with the Standard Regimen (SR), treated with the Enhanced Standard Regimen (ESR), or with FSC Regimens I, IIA, or IIB at various times after treatment, as indicated. For all treatment periods, mice were euthanized 3 days after the last treatment.
Figure 20:
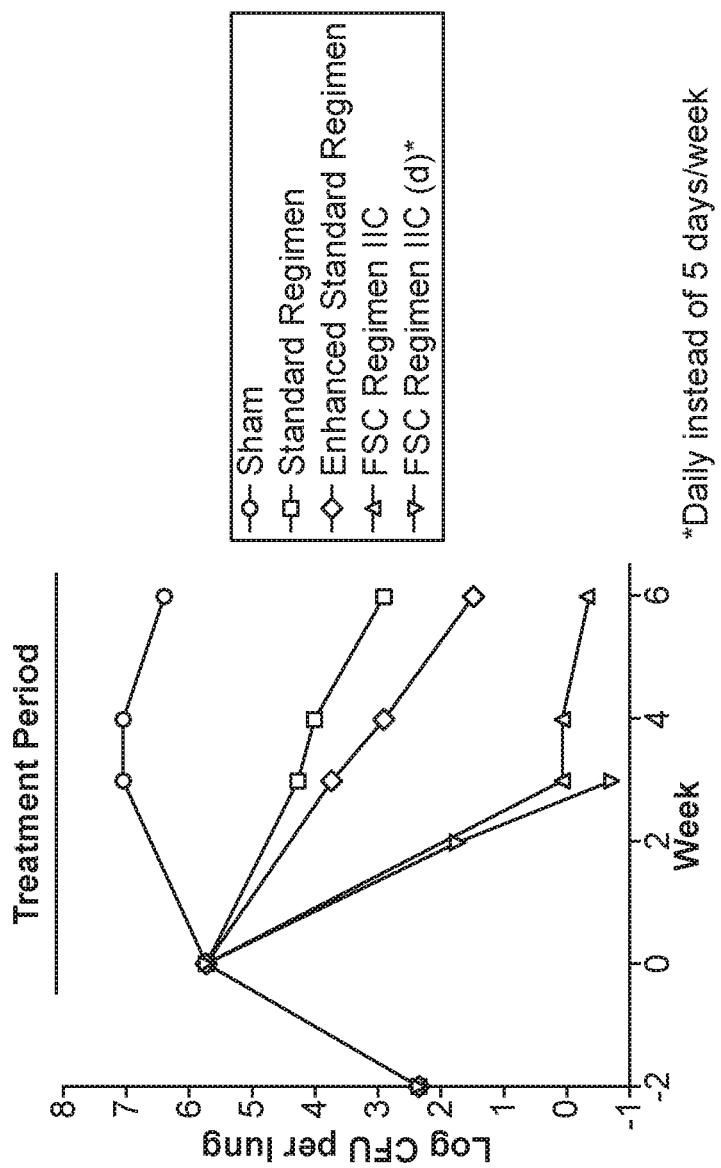
FIG. 20 shows the efficacy of FSC Regimen IIC over 6 weeks of treatment.

FIG. 15 shows the efficacy of FSC Regimens I and IIA/B after 2, 3, 4, 6 or 8 weeks of treatment. In FIG. 15, CFU in the lungs of mice that were sham-treated (Sham), treated with the Standard Regimen (SR), treated with the Enhanced Standard. Regimen (ESR), or with FSC Regimens I, IIA, or IIB at various times after treatment, as indicated. For all treatment periods, mice were euthanized 3 days after the last treatment.

Mice treated with FSC Regimen IIA for 4 weeks had relapse-free cure (see below). At this point, mice treated with the Standard Regimen had about 3.85 log CFU in their lungs.

FIGS. 16-18 show lung CFU of individual mice 3 days after completion of 3, 4 or 6 weeks of treatment with FSC Regimen HA and lung CFU of individual mice 3 months after completion of the treatment.

FIG. 16 shows lung burden 3 days (Efficacy) and 3 months (Relapse) after treatment with FSC Regimen IIA for 3 weeks. FIG. 17 shows lung burden 3 days (Efficacy) and 3 months (Relapse) after treatment with FSC Regimen IIA for 4 weeks. FIG. 18 shows lung burden 3 days (Efficacy) and 3 months (Relapse) after treatment with FSC Regimen IIA for 6 weeks.

Summary and Conclusions.

Mice infected with M. tuberculosis and treated with FSC Regimens I, IIA, and IIB had fewer CFU in their lungs than mice treated with the Standard Regimen or the Enhanced Standard Regimen (High PZA). Mice in the FSC Regimen I, IIA and IIB-treated groups had less lung pathology than mice in the sham group, the group treated with the Standard Regimen, and the group treated with the Enhanced Standard Regimen.

Mice treated with FSC Regimen IIA for 4 weeks had relapse-free cure. At this point, mice treated with the Standard Regimen had about 3.85 log CFU in their lungs. Mice treated with FSC Regimen IIB lowered lung CFU faster than mice treated with FSC Regimen HA. Thus FSC Regimens I, IIA and IIB were markedly superior to the Standard Regimen.

Efficacy and Relapse of FSC Regimens I and BC in a Mouse Model of Pulmonary TB (Mouse In Vivo Experiment 4)

Two hundred and twenty eight eight-week old, female, pathogen-free Balb/c mice were purchased from Harlan. The mice were housed with unlimited access to food and water. After a 7-day quarantine period, mice were infected by aerosol with Mycobacterium tuberculosis, Erdman strain as described. One day later, two mice were euthanized to determine the initial number of bacteria in their lungs. The two mice had 2.30±0.03 log (Mean±SE) CFU of M. tuberculosis/lung (total lung). After two weeks, three mice were euthanized to determine the number of bacteria in the lungs at that time point, and the three mice had 5.68±0.21 log CFU (Mean±SE)/total lung. The mice were then divided into 6 treatment groups as follows:

Efficacy & Relapse Study

Group A: Sham treated with vehicle only by gavage 5x/wk for 3, 4, 6, 8, 12, 16, 20 or 24 wks (40 mice)

Group B: RIF/EMB/INH/PZA (Standard Regimen) by gavage 5x/wk for 3, 4, 6 or 8 wks and then RIF/INH alone until 12, 16, 20 or 24 wks (55 mice)

Group C: RIF/EMB/INH/PZA (Enhanced Standard Regimen) by gavage 5x/wk for 3, 4, 6 or 8 wks and then RIF/NH alone until 12, 16, 20 or 24 wks (55 mice)

Group D: CLZ/EMB/PRO/PZA (FSC Regimen I) by gavage 5x/wk for 8 or 12 wks (20 mice)

Group E: CLZ/EMB/TMC/PZA (FSC Regimen IIC) by gavage 5x/wk for 3, 4 or 6 wks (30 mice)

Group F: CLZ/EMB/TMC/PZA (FSC Regimen IIC) by gavage daily for 2 or 3 wks (20 mice)

Figure 24:
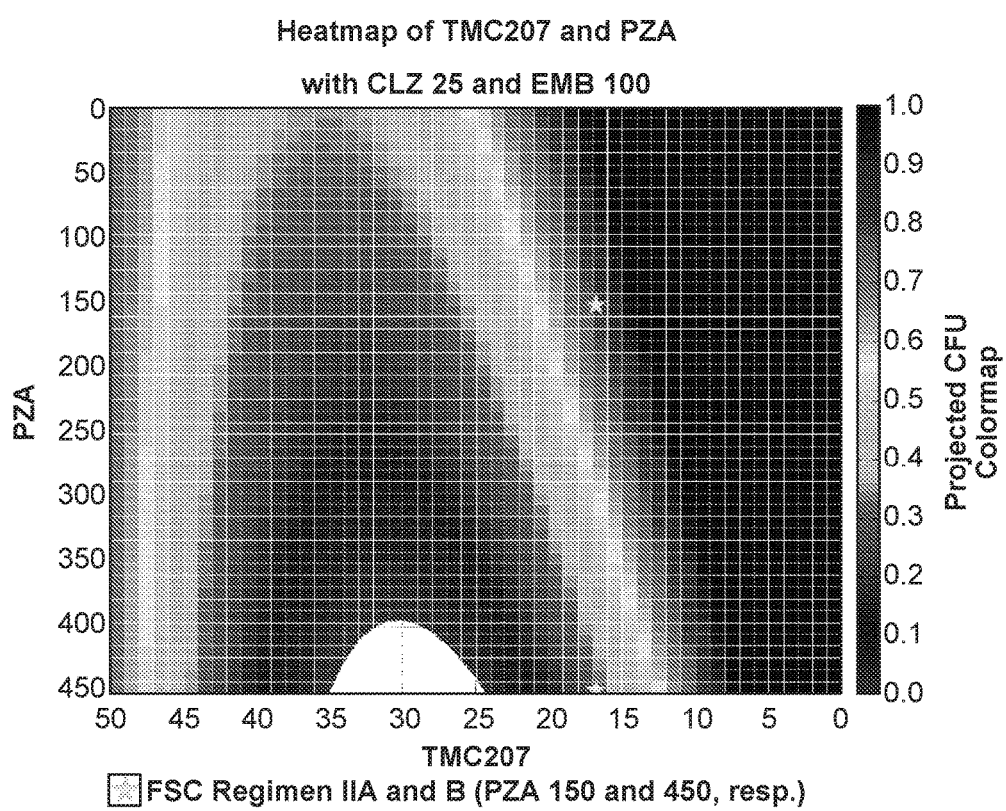
FIG. 24 shows a heatmap for FSC Regimen II.

Drug doses in FSC Regimen IIC were optimized based upon analysis of Mouse in vivo Experiments 2 and 3 (FIG. 24). The optimal doses of TMC207 and PZA were adjusted to about 30 mg/kg and about 450 mg/kg, respectively. Doses of CLZ and EMB were held constant at about 25 mg/kg and about 100 mg/kg, respectively.

The mice were treated by oral gavage five times per week (Monday-Friday) for 2-8 weeks with Standard Regimen, Enhanced Standard Regimen or FSC Regimen IIC, or daily for 2-3 weeks with FSC Regimen IIC as indicated above. The amount of drug in each treatment regimen is as follows:

TABLE 10

List of Standard Regimen controls and Experimental ESC Regimens

| Experimental TB Drug Regimens | Drug Concentration (mg/kg) | | | | |
|---|---|---|---|---|---|
| | CLZ | EMB | PRO | TMC | PZA |
| FSC Regimen I | 25 | 100 | 75 | | 450 |
| FSC Regimen IIC | 25 | 100 | | 30 | 450 |

| Control Standard Regimens | Drug Concentration (mg/kg) | | | |
|---|---|---|---|---|
| | RIF | EMB | INH | PZA |
| Standard Regimen | 10 | 100 | 25 | 150 |
| Enhanced Standard Regimen | 10 | 100 | 25 | 450 |

FIG. 24 shows a heatmap for FSC Regimen II. FIG. 17 shows the scheme of Mouse in vivo data of the experiment. FIG. 18 shows the efficacy of FSC Regimen IIC over 6 weeks of treatment. In FIG. 19, M. tuberculosis burden in the lung over the course of infection and treatment period, where mice were sham-treated (Sham) or treated with the Standard Regimen, Enhanced Standard regimen or FSC Regimen IIC 5 days per week (Monday-Friday), or treated with FSC Regimen IIC daily.

Figure 21:
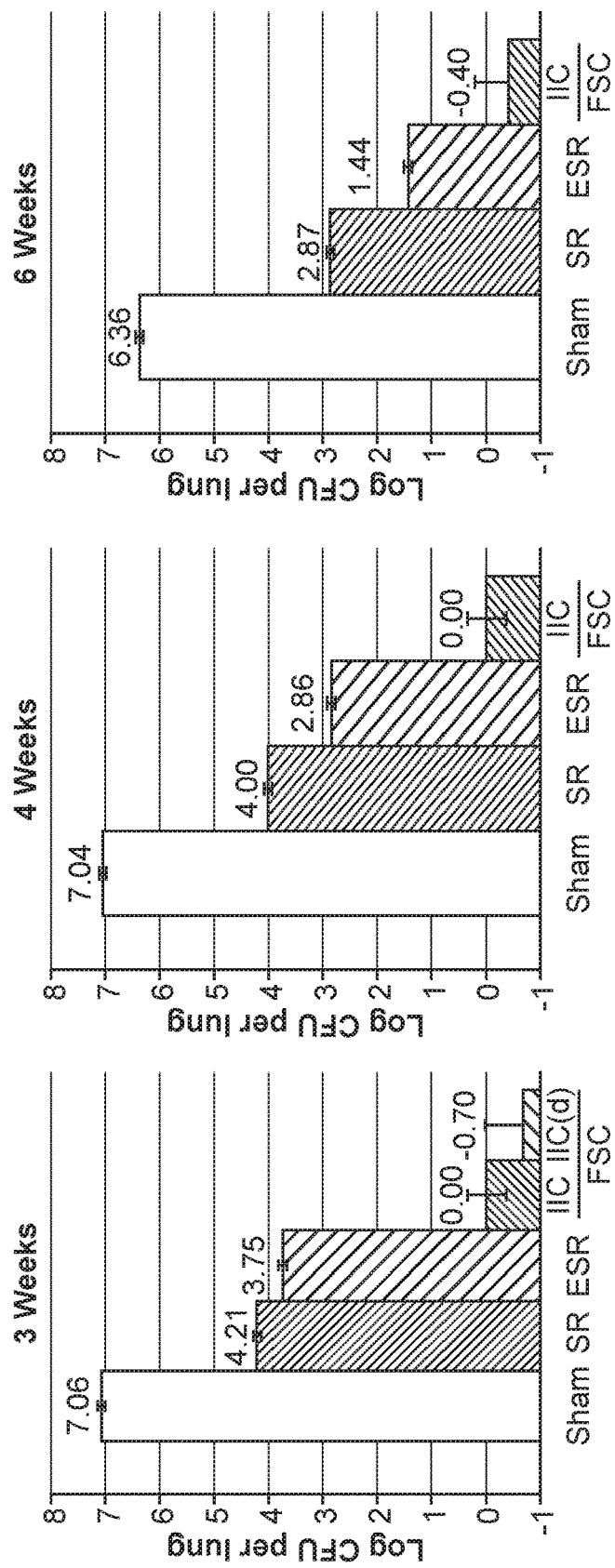
FIG. 21 shows the efficacy of FSC Regimen IIC after 3, 4 or 6 weeks of treatment. CFU in the lungs of mice that were sham-treated (Sham), treated with the Standard Regimen (SR), treated with the Enhanced Standard Regimen (ESR), or treated with FSC Regimen IIC 5 days/week (Monday-Friday) at various times after treatment, as indicated. An additional group was treated with FSC Regimen IIC daily for three weeks. For all treatment periods, mice were euthanized 3 days after the last treatment.
Figure 22:
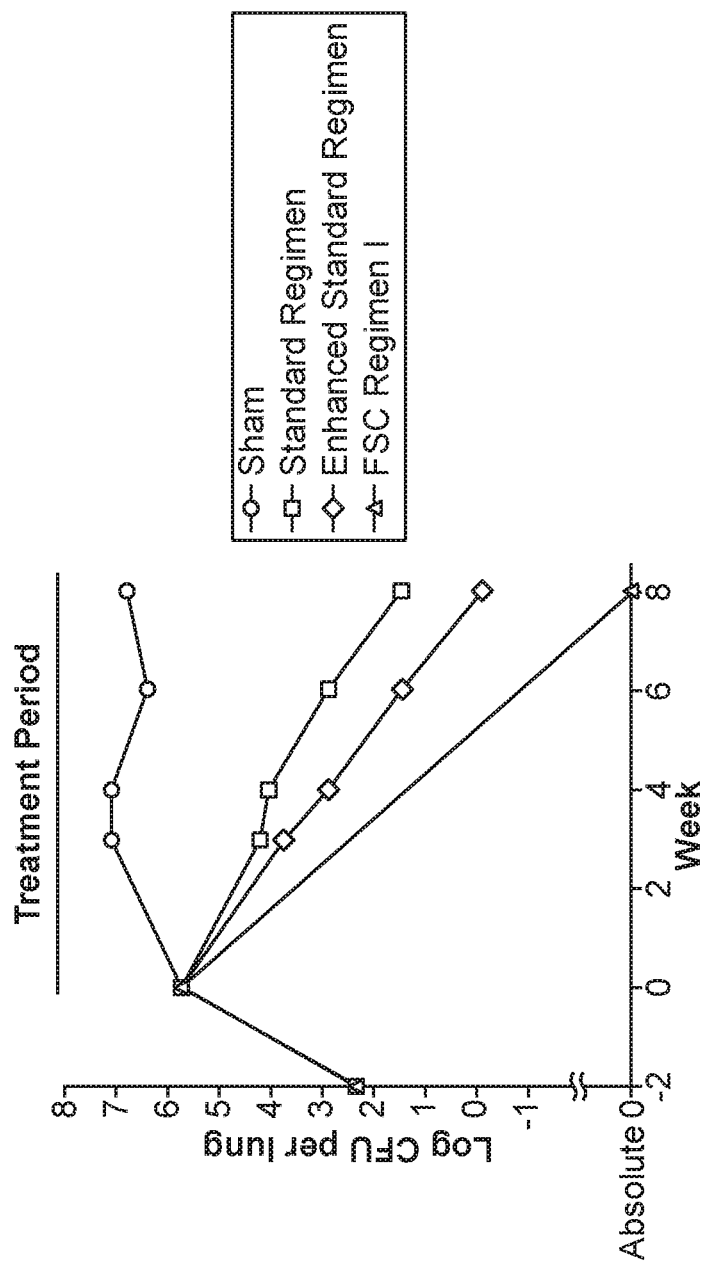
FIG. 22 shows the efficacy of FSC Regimen I after 8 weeks of treatment. *M. tuberculosis* burden in the lung over the course of infection and treatment period, where mice were sham-treated (Sham) or treated with the Standard Regimen, Enhanced Standard regimen or FSC Regimen I, 5 days per week (Monday-Friday). For all treatment periods, mice were euthanized 3 days after the last treatment.

FIG. 21 shows the efficacy of FSC Regimen IIC after 3, 4 or 6 weeks of treatment. In FIG. 21, CFU in the lungs of mice that were sham-treated (Sham), treated with the Standard Regimen (SR), treated with the Enhanced Standard Regimen (ESR), or treated with FSC Regimen IIC 5 days/week (Monday-Friday) at various times after treatment, as indicated. An additional group was treated with FSC Regimen IIC daily for three weeks. For all treatment periods, mice were euthanized 3 days after the last treatment.

FIG. 19 shows the efficacy of FSC Regimen I after 8 weeks of treatment. In FIG. 19, *M. tuberculosis* burden in the lung over the course of infection and treatment period, where mice were sham-treated (Sham) or treated with the Standard Regimen, Enhanced Standard regimen or FSC Regimen I, 5 days per week (Monday-Friday). For all treatment periods, mice were euthanized 3 days after the last treatment.

Figure 23:
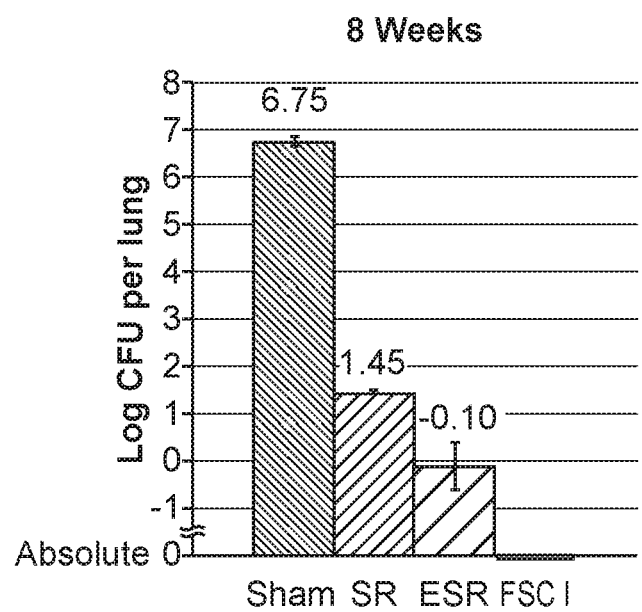
FIG. 23 shows the lung CFU of mice after treatment with the Standard Regimen, Enhanced Standard Regimen, and FSC Regimen I for 8 weeks. CFU in the lungs of mice that were sham-treated (Sham), treated with the Standard Regimen (SR), treated with the Enhanced Standard. Regimen (ESR), or treated with FSC Regimen I, 5 days/week (Monday-Friday) for 8 weeks. For all groups, mice were euthanized 3 days after the last treatment.

FIG. 23 below shows the lung CFU of mice after treatment with the Standard Regimen, Enhanced Standard Regimen, and FSC Regimen I for 8 weeks. In FIG. 21, CFU in the lungs of mice that were sham-treated (Sham), treated with the Standard Regimen (SR), treated with the Enhanced Standard Regimen (ESR), or treated with FSC Regimen I, 5 days/week (Monday-Friday) for 8 weeks. For all groups, mice were euthanized 3 days after the last treatment.

Upon completion of an 8-week treatment with FSC Regimen I, mice were completely sterilized of *M. tuberculosis* infection.

Summary and Conclusions: FSC Regimen IIC.

Mice treated with FSC Regimen IIC had fewer CFU in their lungs than mice treated with the Standard Regimen or the Enhanced Standard Regimen (High PZA). Mice in the FSC Regimen IIC-treated group had less lung pathology than mice in the sham group, the group treated with the Standard Regimen, and the group treated with the Enhanced Standard. Regimen. Mice treated with FSC Regimen IIC for 3 weeks averaged about 1 CFU/lung (Log 0), lower than the amount that resulted in a relapse-free cure with FSC Regimen IIA. [Average of about 3.5 CFU/lung (0.4 logs)] in the previously described experiment. Thus, it is likely that FSC Regimen IIC cures mice (no relapse after cessation of treatment) by 3 weeks. At this point (3 weeks), mice treated with the Standard Regimen had about 4.2 log IIC in their lungs. FSC Regimen IIC administered daily lowered. CFU further at 3 weeks (Log–0.7) than FSC Regimen IIC administered 5 days/week (Log 0). Thus, FSC Regimen IIC is markedly superior to the Standard Regimen and the Enhanced Standard Regimen.

Summary and Conclusions: FSC Regimen I.

Mice treated with FSC Regimen I for 8 weeks had essentially 0 CFU in their entire lungs (Absolute 0) whereas mice treated with the Standard Regimen or the Enhanced Standard Regimen (High PZA) still had CFU in their lungs. Thus, FSC Regimen I cures mice (no relapse after cessation of treatment) by 8 weeks. Mice in the FSC Regimen I-treated group had less lung pathology than mice in the sham group, the group treated with the Standard Regimen, and the group treated with the Enhanced Standard Regimen, Thus, FSC Regimen I is markedly superior to the Standard Regimen and the Enhanced Standard. Regimen.

vii. Embodiments

The following embodiments are within the scope of the disclosure.

Embodiment 1

A pharmaceutical composition comprising a pharmaceutically effective amount of a combination of (a) clofazimine, (b) ethambutol, (c) pyrazinamide, and (d) prothionamide or bedaquiline.

Embodiment 2

The pharmaceutical composition of Embodiment 1, wherein the combination is (a) clofazimine, (b) ethambutol, (c) pyrazinamide, and (d) bedaquiline Embodiment 3

The pharmaceutical composition of Embodiment 1, wherein the combination is (a) clofazimine, (b) ethambutol, (c) pyrazinamide, and (d) prothionamide.

Embodiment 4

A method of treating tuberculosis in a subject in need thereof, comprising
administering to the patient a therapeutically effective amount of a drug combination comprising (a) clofazimine, (b) ethambutol, (c) pyrazinamide, and (d) prothionamide or bedaquiline.

Embodiment 5

The method of Embodiment 4, wherein the combination comprises (a) clofazimine, (b) ethambutol, (c) pyrazinamide, and (d) bedaquiline.

Embodiment 6

The method of Embodiment 4 or 5, wherein the combination comprises (a) clofazimine, (b) ethambutol, (c) pyrazinamide, and (d) prothionamide.

Embodiment 7

The method of one of Embodiments 4-6, wherein one or more of (a)-(d) in the combination is administered sequentially.

Embodiment 8

The method of one of Embodiments 4-7, wherein one or more of (a)-(d) is administered concurrently.

Embodiment 9

The method of one of Embodiments 4-8, wherein the subject is a mammal.

Embodiment 10

The method of Embodiment 9, wherein the mammal is a human.

Embodiment 11

The method of one of Embodiments 4-10, wherein the drug combination consists of (a) clofazimine, (b) ethambutol, (c) pyrazinamide, and (d) prothionamide or bedaquiline.

Embodiment 12

The method of one of Embodiments 4-11, wherein the combination consists of (a) clofazimine, (h) ethambutol, (c) pyrazinamide, and (d) bedaquiline.

Embodiment 13

The method of one of Embodiments 4-11, wherein the combination consists of (a) clofazimine, (b) ethambutol, (c) pyrazinamide, and (d) prothionamide.

Embodiment 14

The method of one of Embodiments 4-13, wherein the tuberculosis is caused by *Mycobacterium tuberculosis*.

Embodiment 15

The method of one of Embodiments 4-14, wherein the tuberculosis is Multi-drug resistant TB.

Embodiment 16

The method of one of Embodiments 4-14, wherein the tuberculosis is Extensively drug-resistant TB.

The invention claimed is:

1. A pharmaceutical composition consisting essentially of a pharmaceutically effective amount of a combination of (a) clofazimine, (b) ethambutol, (c) pyrazinamide, and (d) prothionamide or bedaquiline.

2. A pharmaceutical composition comprising a pharmaceutically effective amount of a combination of (a) clofazimine, (b) ethambutol, (c) pyrazinamide, and (d) bedaquiline.

3. The pharmaceutical composition of claim 1, wherein the combination consists essentially of (a) clofazimine, (b) ethambutol, (c) pyrazinamide, and (d) prothionamide.

4. A method of treating tuberculosis in a subject in need thereof, comprising
administering to the patient a therapeutically effective amount of (i) a drug combination of consisting essentially of (a) clofazimine, (b) ethambutol, (c) pyrazinamide, and (d) prothionamide or bedaquiline or (ii) a drug combination comprising a pharmaceutically effective amount of a combination of (a) clofazimine, (b) ethambutol, (c) pyrazinamide, and (d) bedaquiline.

5. The method of claim 4, wherein one or more of (a)-(d) in the combination is administered sequentially.

6. The method of claim 4, wherein one or more of (a)-(d) is administered concurrently.

7. The method of claim 4, wherein the subject is a mammal.

8. The method of claim 7, wherein the mammal is a human.

9. The method of claim 4, wherein the combination consists essentially of (a) clofazimine, (b) ethambutol, (c) pyrazinamide, and (d) bedaquiline.

10. The method of claim 4, wherein the combination consists essentially of (a) clofazimine, (b) ethambutol, (c) pyrazinamide, and (d) prothionamide.

11. The method of claim 4, wherein the tuberculosis is caused by *Mycobacterium tuberculosis*.

12. The method of claim 4, wherein the tuberculosis is Multi-drug resistant TB.

13. The method of claim 4, wherein the tuberculosis is Extensively drug-resistant TB.

14. The method of claim 4, wherein the tuberculosis is latent TB.

15. The pharmaceutical composition of claim 1, wherein the combination is formulated into a single oral dosage form.

16. The pharmaceutical composition of claim 15, wherein the single oral dosage form is a tablet, gelatin capsule, pill, troche, elixir, or suspension.

17. The method of claim 4, wherein the combination is formulated into a single oral dosage form.

* * * * *